(12) United States Patent
Maitland et al.

(10) Patent No.: US 11,786,641 B2
(45) Date of Patent: Oct. 17, 2023

(54) SHEATHED EMBOLIZATION DEVICE

(71) Applicant: THE TEXAS A&M UNIVERSITY SYSTEM, College Station, TX (US)

(72) Inventors: Duncan J. Maitland, College Station, TX (US); Adam M. Orendain, Tulsa, OK (US)

(73) Assignee: The Texas A&M University System, College Station, TX (US)

( * ) Notice: Subject to any disclaimer, the term of this patent is extended or adjusted under 35 U.S.C. 154(b) by 532 days.

(21) Appl. No.: 16/652,588

(22) PCT Filed: Oct. 10, 2018

(86) PCT No.: PCT/US2018/055164
§ 371 (c)(1),
(2) Date: Mar. 31, 2020

(87) PCT Pub. No.: WO2019/075023
PCT Pub. Date: Apr. 18, 2019

(65) Prior Publication Data
US 2020/0230298 A1 Jul. 23, 2020

Related U.S. Application Data

(60) Provisional application No. 62/570,333, filed on Oct. 10, 2017.

(51) Int. Cl.
*A61L 31/14* (2006.01)
*A61L 31/06* (2006.01)
(Continued)

(52) U.S. Cl.
CPC ........ *A61L 31/06* (2013.01); *A61B 17/12113* (2013.01); *A61B 17/12118* (2013.01);
(Continued)

(58) Field of Classification Search
CPC ........ A61F 2/07; A61F 2/82; A61F 2002/823; A61F 2002/068; A61L 2400/16;
(Continued)

(56) References Cited

U.S. PATENT DOCUMENTS 6,152,144 A 11/2000 Lesh et al.
8,876,895 B2 * 11/2014 Tuval .................... A61F 2/2436
623/2.14

(Continued)

FOREIGN PATENT DOCUMENTS

CN 103110444 A 5/2013
CN 104053409 A 9/2014
(Continued)

OTHER PUBLICATIONS

European Patent Office, Communication Pursuant to Article 94(3) dated Jul. 26, 2022 in European Patent Application No. 18796221.2 (7 pages).
(Continued)

*Primary Examiner* — Dinah Baria
(74) *Attorney, Agent, or Firm* — TROP, PRUNER & HU, P.C.

(57) ABSTRACT

An embodiment includes an apparatus comprising: a shape memory polymer (SMP) foam having an outside surface; and a membrane that encapsulates at least 50% of the outside surface of the SMP foam; wherein (a) the SMP foam includes a thermoset SMP, and (b) the membrane includes a thermoplastic polymer. Other embodiments are addressed herein.

9 Claims, 27 Drawing Sheets

(51) Int. Cl.
  A61F 2/07 (2013.01)
  A61B 17/12 (2006.01)
  A61L 31/18 (2006.01)
(52) U.S. Cl.
  CPC .......... *A61B 17/12181* (2013.01); *A61F 2/07* (2013.01); *A61L 31/146* (2013.01); *A61L 31/148* (2013.01); *A61L 31/18* (2013.01); *A61L 2300/606* (2013.01); *A61L 2400/16* (2013.01); *A61L 2430/36* (2013.01)
(58) Field of Classification Search
  CPC ...... A61L 31/146; A61L 31/18; A61L 31/148; A61L 31/06; A61B 17/12113; A61B 17/12118; A61B 17/12181
  See application file for complete search history.

(56) References Cited

U.S. PATENT DOCUMENTS

| | | | | |
|---|---|---|---|---|
| 8,993,831 | B2* | 3/2015 | Sharma | A61L 24/046 514/772.3 |
| 9,023,074 | B2 | 5/2015 | Teobald et al. | |
| 10,537,426 | B2 | 1/2020 | Iamberger et al. | |
| 10,575,948 | B2 | 3/2020 | Iamberger et al. | |
| 2012/0158034 | A1 | 6/2012 | Wilson et al. | |
| 2013/0317541 | A1 | 11/2013 | Singhal et al. | |
| 2014/0081414 | A1* | 3/2014 | Hall | A61L 31/048 264/413 |
| 2015/0313606 | A1 | 11/2015 | Wilson et al. | |
| 2019/0015108 | A1 | 1/2019 | Maitland et al. | |
| 2021/0068947 | A1* | 3/2021 | Nash | A61L 27/06 |

FOREIGN PATENT DOCUMENTS

| | | |
|---|---|---|
| CN | 105246540 A | 1/2016 |
| CN | 105907059 A | 8/2016 |
| CN | 106999271 A | 8/2017 |
| JP | 2016518155 A | 6/2016 |
| WO | 2017040918 A1 | 3/2017 |

OTHER PUBLICATIONS

European Patent Office, Communication and Written Opinion of the International Searching Authority, dated May 19, 2020, in European patent application No. 18 796 221.2, 9 pages total.
International Search Report and Written Opinion, issued in International Application No. PCT/US2018/055164, dated Jan. 24, 2019, nine pages.
Orendain, "Design, Fabrication, and Testing of a Sheathed Embolization Device," Master of Science, Texas A&M University, Dec. 2017, 100 pages.
Hasan et al., "Modification of Shape Memory Polymer Foams Using Tungsten, Aluminum Oxide, and Silicon Dioxide Nanoparticles," RSC Adv. 2016; 6(2): 918-927.
Horn et al., "Comparison of Shape Memory Polymer Foam Versus Bare Metal Coil Treatments in an in vivo Porcine Sidewall Aneurysm Model," published online Jun. 3, 2016, Wiley Online Library, pp. 1892-1905.
Hasan et al., "Porous Shape Memory Polymers: Design and Application," published online Jan. 10, 2016, Journal of Polymer Science, Part B: Polymer Physics 2016, 54, 1300-1318.
Landsman et al., "Design and Verification of a Shape Memory Polymer Peripheral Occlusion Device," Journal of the Mechanical Behavior of Biomedical Materials 63 (2016), 195-206.
Rodriguez et al., "In Vivo Response to an Implanted Shape Memory Polyurethane Foam in a Porcine Aneurysm Model," Journal of Biomedical Materials Research Part A, May 2014, vol. 102A, Issue 5, pp. 1231-1242.
Romero et al., "Cardiac Imaging for Assessment of Left Arterial Appendage Stasis and Thrombosis," Nature Reviews, Cardiology, vol. 11, Aug. 2014, pp. 470-480.
Holmes et al., "Percutaneous Closure of the Left Atrial Appendage Versus Warfarin Therapy for Prevention of Stroke in Patients With Atrial Fibrillation: a Randomised Non-Inferiority Trial," The Lancet, vol. 374, Aug. 15, 2009, pp. 534-542.
Lloyd-Jones et al., "Lifetime Risk for Development of Atrial Fibrillation," The Framingham Heart Study, 2004, pp. 1042-1046.
Romero et al., "Left Atrial Appendage Closure Devices," Clinical Medicine Insights: Cardiology, 2014: 8, pp. 45-52.
Akinapelli et al., "Left Atrial Appendage Closure—the WATCH-MAN Device," Current Cardiology Reviews, 2015, vol. 11, No. 4, pp. 334-340.
Singh et al., "Left Atrial Appendage Closure," Current Cardiology Reports, 2010, vol. 12, Issue 5, pp. 413-421.
Lin et al., "Left Atrial Appendage Closure," Progress in Cardiovascular Diseases, vol. 58, Issue 2, 2015, pp. 195-201.
Bergmann et al., "Left Atrial Appendage Closure for Stroke Prevention in Non-Valvular Atrial Fibrillation: Rationale, Devices in Clinical Development and Insights into Implantation Techniques," Expert Review, Interventions for Structural Heart Disease, EuroIntervention 2014; 10; 497-504.
Saw et al., "Percutaneous Left Atrial Appendage Closure: Procedural Techniques and Outcomes," JACC: Cardiovascular Interventions, vol. 7, Issue 11, Nov. 2014, pp. 1205-1220.
"Particulate Matter in Injections," Revision Bulletin, Offical Jul. 1, 2012.
"Non-Clinical Engineering Tests and Recommended Labeling for Intravascular Stents and Associated Delivery Systems," Guidance for Industry and FDA Staff, Center for Devices and Radiological Health, dated Apr. 18, 2010.
Kastrup et al., "Early Outcome of Carotid Angioplasty and Stenting with and Without Cerebral Protection Devices," A Systematic Review of the Literature, Stroke, vol. 34, Issue 3, 003, pp. 813-819.
Hasan et al., "Effects of Isophorone Diisocyanate on the Thermal and Mechanical Properties of Shape-Memory Polyurethane Foams," Macromolecular Chemistry and Physics, vol. 215, Issue 24, 2014, pp. 2420-2429.
Rodriguez et al., "Reticulation of Low Density Shape Memory Polymer Foam with an In Vivo Demonstration of Vascular Occlusion," Journal of the Mechanical Behavior of Biomedical Materials, vol. 40, 2014, pp. 102-114.
Nash et al., "Cold Plasma Reticulation of Shape Memory Embolic Tissue Scaffolds," Macromolecular Rapid Communications, vol. 37, 2016, pp. 1945-1951.
Singhal et al., "Ultra Density and Highly Crosslinked Biocompatible Shape Memory Polyurethane Foams," Journal of Polymer Science, Part B, Polymer Physics, vol. 50(10), 724-737.
Small IV et al., "Biomedical Applications of Thermally Activated Shape Memory Polymers," Journal of Materials Chemistry, vol. 20, 2010, pp. 3356-3366.
Muschenborn et al., "Porous Media Properties of Reticulated Shape Memory Polymer Foams and Mock Embolic Coils for Aneurysm Treatment," BioMedical Engineering Online 2013, 12:103, p. 1-13.
Nathan et al., "Particulate Release From Nanoparticle-Loaded Shape Memory Polymer Foams," Journal of Medical Devices, vol. 11, 2017, nine pages.
Möbius-Winkler et al. "Percutaneous Left Atrial Appendage Closure: Technical Aspects and Prevention of Periprocedural Complications with the watchman device," World Journal of Cardiology, vol. 7, Issue 2, 2015, pp. 65-75.
Swaans et al., "Catheter Ablation in Combination With Left Atrial Appendage Closure for Atrial Fibrillation," Journal of Visualized Experiments, vol. 72, e3818, 2013, nine pages.
Vaidya et al., "An Overview of Embolic Agents," Seminar in Interventional Radiology, vol. 25, No. 3, 2008, pp. 204-215.
Rodés-Cabau et al., "Transcatheter Closure of the Left Atrial Appendage: Initial Experience with the Amplatzer Cardiac Plug Device," Catheterization and Cardiovascular Interventions, vol. 76, Issue 2, 2010, pp. 186-192.
Quizhpe et al., "Left Atrial Appendage Closure With the Watchman Device," Sociedade Brasileria de Hemodinâmica e Cardiologia Intervencionista, vol. 22, Issue 1, 2014, pp. 56-63.

(56) References Cited

OTHER PUBLICATIONS

Freixa et al., "The Amplatzer Cardiac Plug 2 for Left Atrial Appendage Occlusion: Novel Features and First in-Man Experience," EuroIntervention, vol. 8, No. 9, 2013, pp. 1094-1098.

Rodriguez et al., "Opacification of Shape Memory Polymer Foam Designed for Treatment of Intracranial Aneurysms," Annals of Biomedical Engineering, 2012, vol. 40(4), 883-897.

Win et al., "Microemboli Generation, Detection and Characterization During CPB Procedures in Neonates, Infants, and Small Children," American Society of Artificial Internal Organs Journal, 2008, pp. 486-490.

Siewiorek et al., "The Angioguard Embolic Protection Device," Expert Rev Med Devices, 2008, vol. 5(3), pp. 287-296.

Order et al., "Comparison of 4 Cerebral Protection Filters for Carotid Angioplasty: An In Vitro Experiment Focusing on Carotid Anatomy," Journal of Endovascular Therapy, 2004, vol. 11, pp. 211-218.

Truckenmüller et al., "Thermoforming of Film-Based Biomedical Microdevices," Advanced Materials, 2011, vol. 23, 1311-1329.

Hogan et al., "Transcatheter closure of patent ductus arteriosus in a dog with a peripheral vascular occlusion device," Journal of Veterinary Cardiology, 2006, vol. 8, pp. 139-143.

Violaris et al., "Endovascular stents: a 'break through technology', future challenges," International Journal of Cardiac Imaging vol. 13, 1997, pp. 3-13.

Wu et al., "Novel Microporous Films and Their Composites," Journal of Engineered Fibers and Fabrics, vol. 2, Issue 1, 2007, pp. 49-59.

Singhal et al., "Controlling the Actuation Rate of Low-Density Shape-Memory Polymer Foams in Water," Macromolecular Chemistry and Physics, 2013, vol. 214, 1204-1214.

Chen et al., "Structure and Properties of Polyurethane/Nanosilica Composites," Journal of Applied Polymer Science, vol. 95, 2005, pp. 1032-1039.

Marois et al., "Biocompatibility of Polyurethanes," Madame Curie Bioscience Database [Internet], Austin (TX), Landes Bioscience; 2000-2013.

Bartolo et al., "Bio-Materials and Prototyping Applications in Medicine," Jan. 2008.

Rosset et al., "OsiriX: An Open-Source Software for Navigating in Multidimensional DICOM Images," Journal of Digital Imaging, vol. 17, No. 3, 2004, pp. 205-216.

Fedorov et al., "3D Slicer as an Image Computing Platform for the Quantitative Imaging Network," Magn Reson Imaging, 2012, vol. 30(9), pp. 1323-1341.

Cignoni et al., "MeshLab: an Open-Source Mesh Processing Tool," Eurographics Italian Chapter Conference, 2008.

Kawasaki et al., "Electron Microscopic Evaluations of Clot Morphology During Thrombelastography," International Anesthesia Research Society. 2004, vol. 99, pp. 1440-1444.

Akin et al., "Left atrial appendage occlusion: A better alternative to anticoagulation?", World Journal of Cardioliology, 2017, vol. 9(2), pp. 139-146.

Rajwani et al., "Left Atrial Appendage Eccentricity and Irregularity are Associated With Residual Leaks After Percutaneous Closure," JACC: Clinical Electrophysiology, 2015, vol. 1, No. 6, pp. 478-485.

Baldez et al., "Employment of polyurethane foam for the adsorption of Methylene Blue in aqueous medium," Journal of Hazardous Materials, vol. 159, 2008, pp. 580-586.

Chung et al., "Predicting Peri-Device Leakage of Left Atrial Appendage Device Closure Using Novel Three-Dimensional Geometric CT Analysis," Journal Cardiovascular Ultrasound, 2015, vol. 23(4), pp. 211-218.

Kapur et al., "Left Atrial Appendage Closure Devices for Stroke Prevention," Arrhythmia & Electrophysiology Review, 2014, vol. 3(1), pp. 25-29.

Mousa et al., "Current update of cerebral embolic protection devices," Journal of Vascular Surgery, 2012, pp. 1429-1437.

Moody et al., "Brain Microemboli Associated With Cardiopulmonary Bypass: A Histologic and Magnetic Resonance Imaging Study," The Annals of Thoracic Surgery, vol. 59, Issue 5, 1995, pp. 1304-1307.

"Medical Grade Aliphatic Polyurethan/Urethan/TPU Film," DelStar Technologies, Inc., 2015.

Japanese Patent Office, Notice of Reason(s) for Refusal dated Sep. 27, 2022 in Japanese Patent Application No. 2020-520286 (12 pages).

Chinese Patent Office, Office Action dated Mar. 4, 2023 in Chinese Patent Application No. 201880079784.8 (20 pages).

Japanese Patent Office, Office Action dated Apr. 4, 2023 in Japanese Patent Application No. 2020-520286 (9 pages).

* cited by examiner

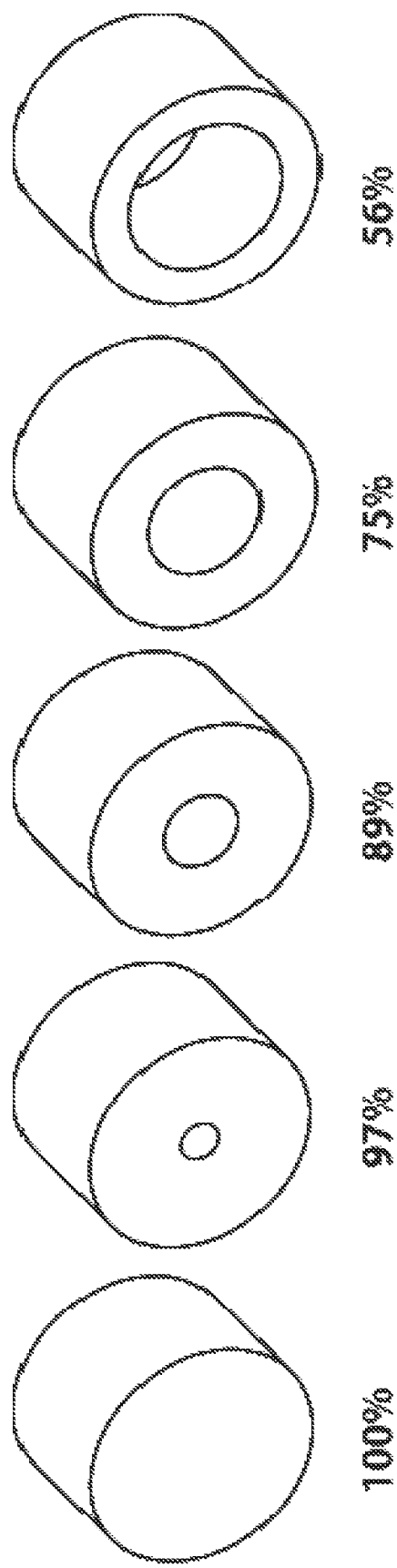

Figure 1

H40 SMP foams (30 mm OD x 20 mm length) with increasing bore diameter. From left to right, 0, 5, 10, 15, and 20 mm bore diameters. The percent below the foam indicates the volume relative to the non-bored foam.

100%   97%   89%   75%   56%

| Pore Size (µm) | ~1000 (Small) | | | | | ~1500 (Medium) | | | | | ~1800 (Large) | | | | |
|---|---|---|---|---|---|---|---|---|---|---|---|---|---|---|---|
| Bore Size (mm) | 0 | 5 | 10 | 15 | 20 | 0 | 5 | 10 | 15 | 20 | 0 | 5 | 10 | 15 | 20 |

Figure 2

Investigated H40 foams. Small, medium, and large (S, M, and L) designations correspond to pore sizes of approximately 1000, 1500, and 1800 µm, respectively. Foams of each pore size will have 0 to 20 mm bores in the center.

| Pore Classification | Foam Batch | Axial Pore Size (μm) | Transverse Pore Size (μm) |
|---|---|---|---|
| Small (~1000 μm) | 16011RCHAE01 | 1216 ± 189 | 906.6 ± 114 |
| | 160701RCHPEDGF06 | 1047 ± 133 | 1051 ± 228 |
| | 160525PEDAE01 | 1079 ± 135 | 813.9 ± 114.4 |
| Medium (~1500 μm) | 160511PEDMH02 | 1537 ± 186 | 1024.5 ± 121.7 |
| | 160515PEDAE03 | 1527.83 ± 252 | 1022.5 ± 173 |
| | 150913RCHMH04 | 1244.9 ± 245.1 | 1318.2 ± 175.15 |
| | 161004PEDAE01 | 1564 ± 300.5 | 1089.9 ± 195 |
| Large (~1800 μm) | 160929PEDAE01 | 1739.4 ± 359 | 927.8 ± 170 |

Axial and transverse pore sizes of foam batches

Figure 4

| Pore Size | Average Dry $T_g$ (°C) | Std. Dev. | Average Wet $T_g$ (°C) | Std. Dev. |
|---|---|---|---|---|
| Small Pore | 59.53 | 1.45 | 13.52 | 1.84 |
| Medium Pore | 61.65 | 2.40 | 15.34 | 2.99 |
| Large Pore | 63.24 | 0.29 | 15.27 | 0.99 |

Wet and dry $T_g$ temperatures for small, medium, and large pore foams.

Figure 5

Final crimped diameter as a function of pore and bore diameter. The ID of a 12 Fr catheter is taken as 3.75 mm (N ≥ 3).

| Bore Size (mm) | Small Pore | Medium Pore | Large Pore |
|---|---|---|---|
| 0 | 7.31 ± 0.12 | 7.68 ± 0.15 | 7.49 ± 0.01 |
| 5 | 7.85 ± 0.90 | 7.92 ± 0.20 | 7.73 ± 0.06 |
| 10 | 7.90 ± 0.31 | 8.30 ± 0.33 | 8.16 ± 0.22 |
| 15 | 8.60 ± 0.41 | 8.97 ± 0.17 | N/A |
| 20 | 9.99 ± 0.07 | 10.42 ± 0.19 | N/A |

Figure 7

The average expansion ratios ± standard deviation of H40 foams as a function of bore and pore size (N ≥ 3). N/A corresponds to insufficient data due to limited availability of foams.

Figure 8(A): Expansion profiles as a function of pore and bore diameter (Small Pore Foam).
Figure 8(B): Expansion profiles as a function of pore and bore diameter (Medium Pore Foam).

| Design Criteria | Design Requirement |
| --- | --- |
| Compatible with current delivery systems | Deliverable through a 12Fr catheter |
| Able to treat large LAA's | Expands to a diameter of 30 mm |
| Delivery mechanism | Simple and easy mechanism to delivery and deploy device |
| Radiopacity | Must be visible under fluoroscopy |
| Particulate reduction | A significant reduction in particulates between a sheathed and non-sheathed embolization device |
| Occlusion | Allows blood and cellular infiltration throughout the foam matrix |
| Wall apposition | Device should conform to the irregularly shaped LAA wall |
| Cost and ease of manufacturing | Devices should be assembled in a cost and time efficient manner |
| Integration with hard materials | The device should have potential to integrate with nitinol or predicate devices to expand the clinical and commercial utility |
| Ability to be recaptured | Should be retractable to be enticing to clinicians |
| Biocompatibility and hemocompatibility | Materials and device should: illicit a healing response, form an endothelial layer, and not form an unstable, undesired thrombus |

Design considerations for the development of SED.

Figure 9

| Polymer Membrane | Mesh Pore Size (μm) | Cardiovascular Application |
|---|---|---|
| Polyester | 30 | Blood filter (ex vivo) |
| | | Cardiac support device, Left atrial appendage closure device, Endovascular stent-graft, Vascular Prosthesis |
| PTFE | N/A | Embolic vena cava filter, Endovascular stent-graft, Vascular Prosthesis, Left atrial appendage closure device |
| FEP | N/A | Embolic vena cava filter |
| UHMWPE | N/A | Left atrial appendage closure device |
| Polyurethane | 80 – 140 | Embolic protection device |
| PET | 160 – 1016 | Left atrial appendage closure devices |
| ePTFE | N/A | Left atrial appendage closure devices |
| Poly(carbonate) | N/A | Left atrial appendage closure devices |
| Nylon | N/A | Left atrial appendage closure devices |

Medical fibers and biotextiles used in embodiments. Abbreviations PTFE: Polytetrafluoroethylene; FEP: Fluorinated ethylene propylene polymer; ePTFE: Expanded polytetrafluoroethylene; PET: Polyethylene terephthalate; UHMWPE: Ultra high molecular weight polyethylene

Figure 11

| Membrane Material | Thickness (μm) | Cost per device ($) | Processing Ability | Pore Size (μm) | Use in 510(k) submissions (or medical grade) |
|---|---|---|---|---|---|
| TPU films | 23 – 28 | ~0.01 | ✓ | Non-porous | Yes |
| PET | 40 – 140 | 0.44 | ✓ | 40 | No |
| UHMWPE | 127 – 254 | 0.18 | ✗ | Non-porous | No |
| PTFE | 127 – 254 | 0.36 | ✗ | Non-porous | No |
| ePTFE | 10 – 1140 | N/A | ✗ | Non-porous | Yes |

Comparison of investigated membrane materials.

Figure 12

Figure 13A
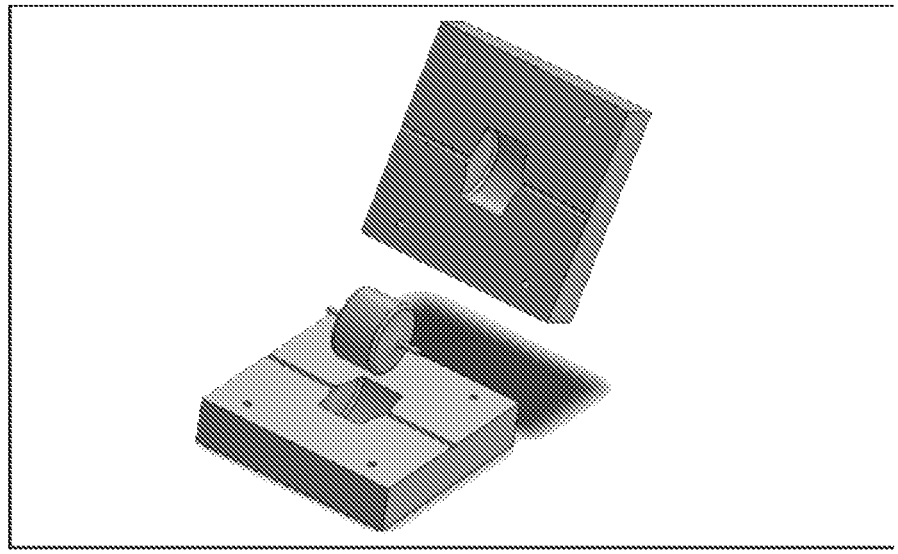
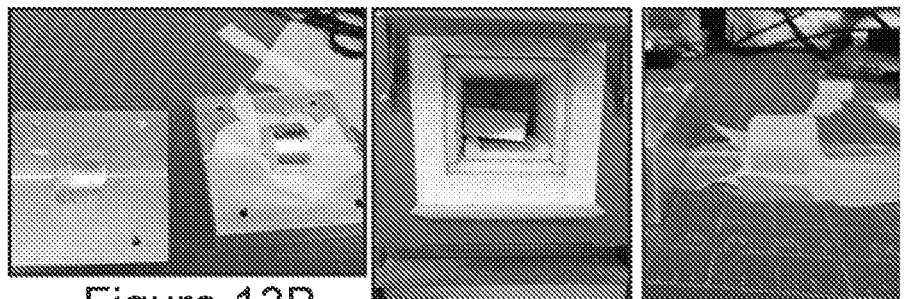
Figure 13B  Figure 13C  Figure 13D
Figure 13(A) SolidWorks design of fixture to mechanically thermoform plastic membranes.
Figure 13 (B) Placement of membranes into fixture.
Figure 13 (C) Placement of fixture into furnace.
Figure 13 (D) Fixed three-dimensional membrane as a result of thermoforming.

Delivery detachment components. Asterisk indicates laser weld.

A crimped SED (left) and an expanded SED (right).

| Device component | Component Description |
|---|---|
| Occlusion Member | H40 SMP foam |
| Membrane | Porous TPU films (pore diameter = 261 μm; 10.54% porosity; thickness < 30 μm) |
| Marker Bands | SS tubes (5 mm length; 2.92 mm OD) on the proximal and distal ends of device |
| Delivery Mechanism | Screw-release; a threaded delivery cable interfaces with threaded marker bands on the device |
| Delivery Cable | A generic SS torque cable |

Figure 16

Summary of final device composition for an embodiment.

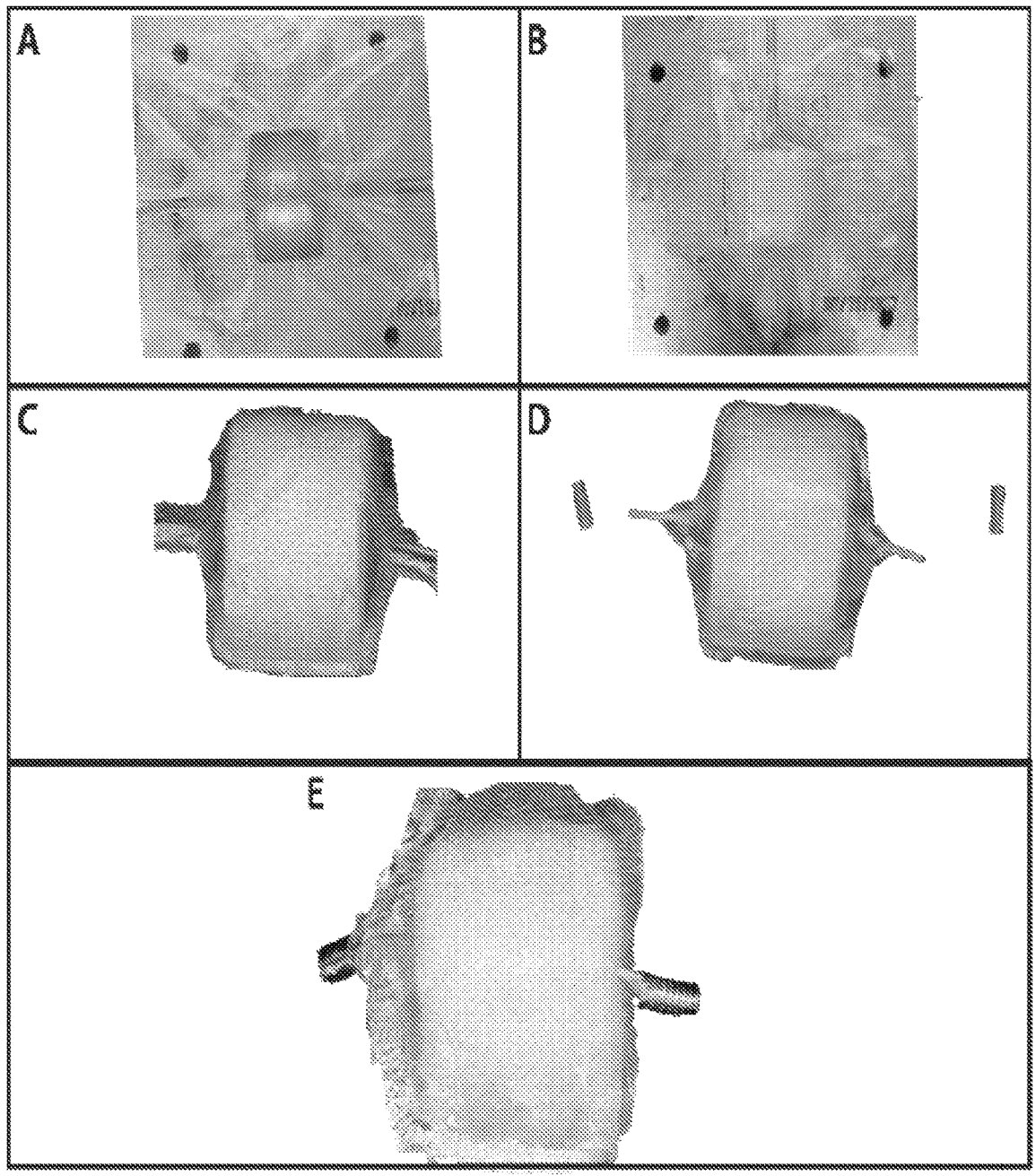

Fabrication of a SED.

Figures 17A and 17B: A thin thermoplastic film and foam is placed into an aluminum fixture. The fixture is then placed into a furnace to heat seal the film together.

Figure 17C: The edges of the film are trimmed by laser or razor.

Figure 17D: The ends of the film are crimped to easily attach and epoxy SS marker bands.

Figure 17E: The fully encapsulated foam with SS marker bands.

Figure 17

Light microscope images of laser created pores in TPU film; Figure 18(A) 100x magnification Figure 18(B) 200x magnification.

ATR FTIR spectra of H40 neat films and AU25, EU28, and EU29 TPU films.

DSC thermograms showing the first heating cycle. Arrowheads indicate location of $T_G$.

| SED Description | Dry Weight (g) | Membrane | Type of Blood | ACT (s) |
|---|---|---|---|---|
| Non-porous SED | 0.486 | Non-porous TPU film | Activated | 161 |
| Porous SED | 0.502 | Porous TPU film | Activated | 122 |
| Non-porous SED | 0.488 | Non-porous TPU film | Citrated | >1500 |
| Porous SED | 0.498 | Porous TPU film | Citrated | >1500 |

Description of SED samples used herein corresponding to the bovine blood.

Figure 21

Crimped diameter of SEDs as a function of bore diameter. SEDs were fabricated with foams with medium sized pores, and crimped over a 0.008" nitinol wire (N = 2).

| Sample Description | Blood Status | Initial Mass (g) | Dried Mass (g) | % Change |
|---|---|---|---|---|
| Non-porous SED | Activated | 0.486 | 0.568 | 16.9 |
| Porous SED | Activated | 0.502 | 1.23 | 145 |
| Non-porous SED | Citrated | 0.488 | 1.31 | 168 |
| Porous SED | Citrated | 0.498 | 1.49 | 201 |
| Control foam | N/A | 0.420 | 0.410 | -2.42 |

Results of submerged SED samples in bovine blood (N = 1).

Figure 23

| Sample (N = 2) | ≥ 10 μm | ≥ 25 μm |
|---|---|---|
| Particle-free water | 33.00 ± 8.485 | 8.500 ± 2.121 |
| Foam | 6057 ± 567.1 | 1805 ± 65.76 |
| Porous SED | 896.5 ± 129.4 | 372.0 ± 110.3 |
| Non-porous SED | 1934 ± 183.1 | 680.0 ± 306.9 |

Mean ± standard deviation of particles counted for particles ≥ 10 μm and ≥ 25 μm.

Figure 24

Number of particulates counted from particle-free water, SMP foam, a non-porous SED, and a porous SED. Asterisks indicate a significant difference ($p < 0.05$) when compared to SMP foam.

SEM image of particle on filter membrane.

SEM image filter membrane.

| Mechanical Property | AU25 TPU Film | EU28 TPU Film | EU29 TPU Film |
|---|---|---|---|
| Thickness (μm) | 23 | 28 | 27 |
| Tensile Strength (MPa) | 0.079 | 0.10 | 0.079 |
| Elongation at Break % | 400 | 650 | 500 |

Figure 27

Mechanical properties of TPU film compositions used to fabricate SEDs.

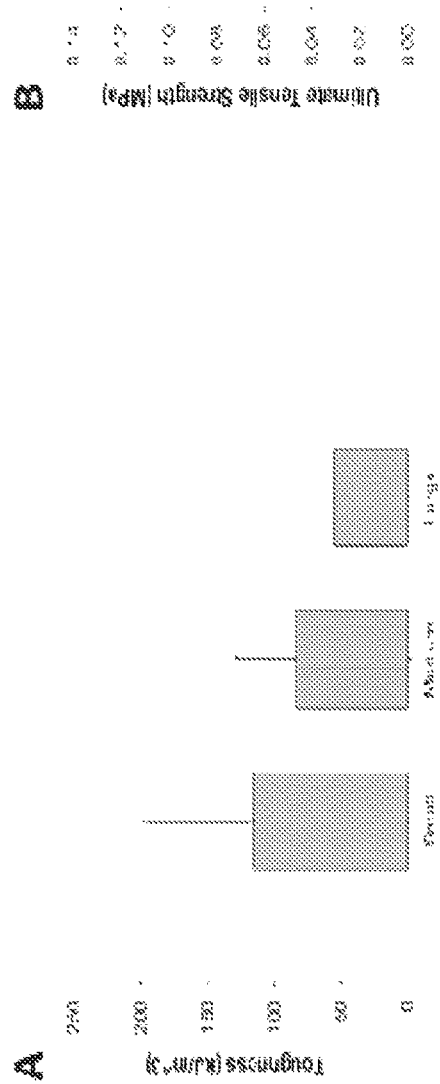
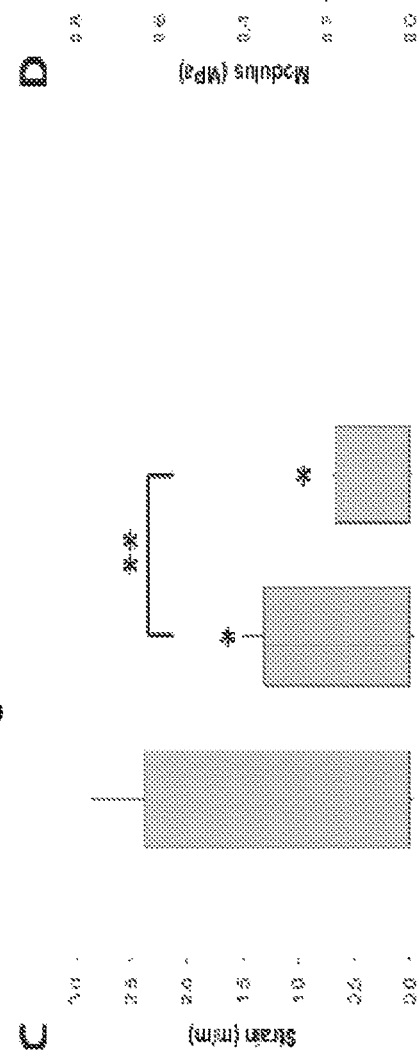
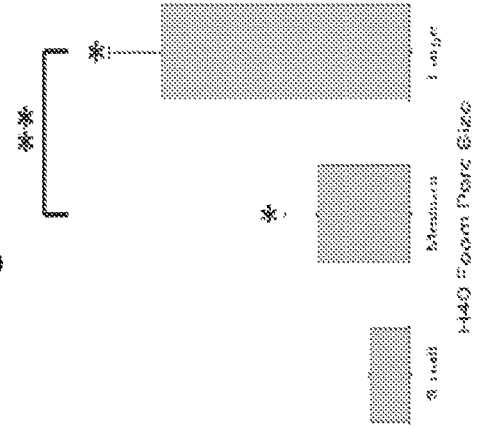
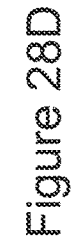
Figure 28(A) Toughness. Figure 28(B) ultimate tensile strength. Figure 28(C) strain at break. Figure 28(D) modulus of H40 foam for varying pore sizes. Small, medium, and large corresponds to a pore size of 1000, 1500, and 1800 μm, respectively. Mean ± standard deviation displayed; N ≥ 4; *$p<0.05$ relative to small pore foam; **$p<0.05$ between the bracketed groups.

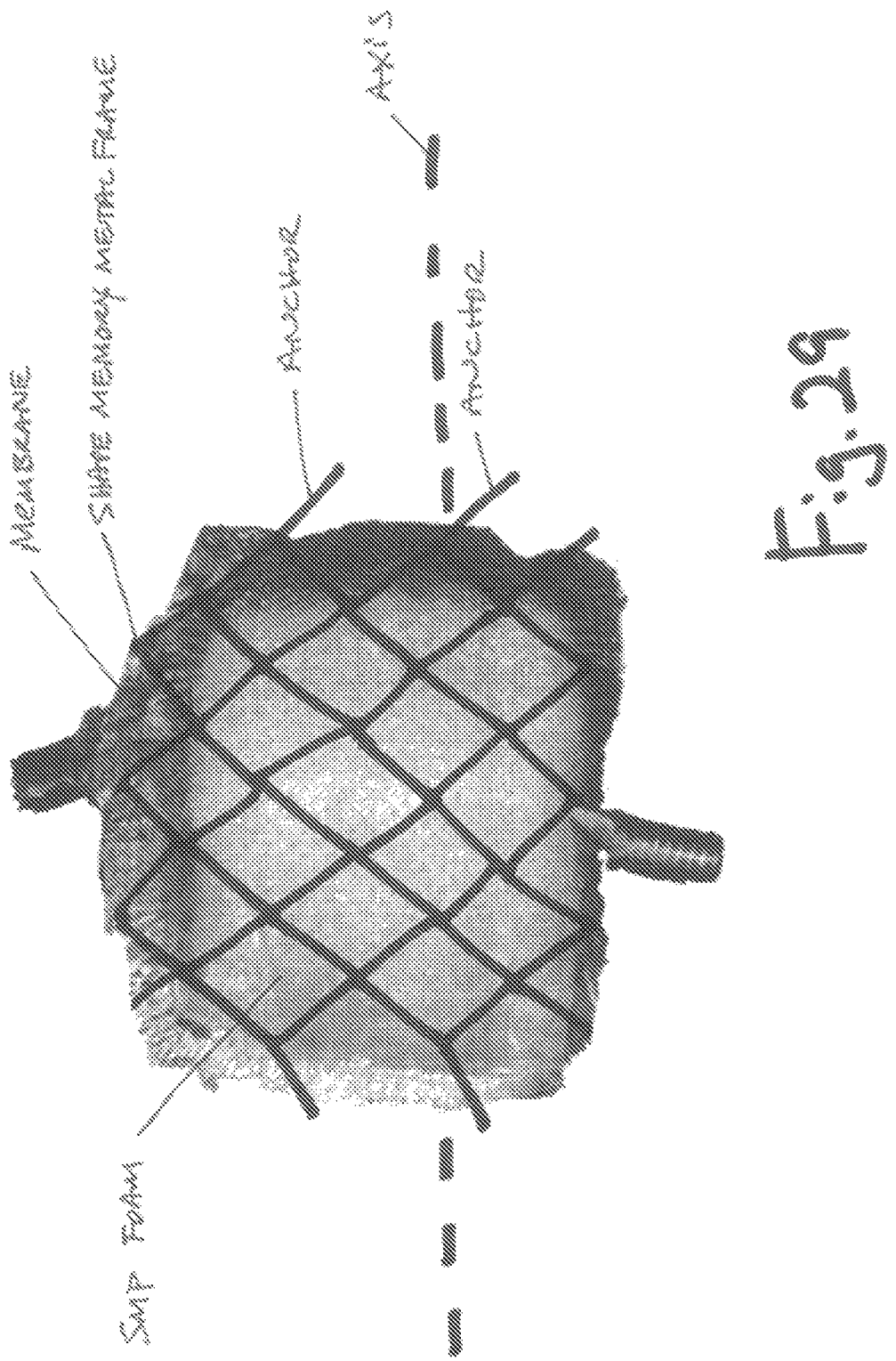

SHEATHED EMBOLIZATION DEVICE

CROSS-REFERENCE TO RELATED APPLICATION

This application claims priority to U.S. Provisional Patent Application No. 62/570,333 filed on Oct. 10, 2017 and entitled "Embolization Device with Membrane", the content of which is hereby incorporated by reference.

STATEMENT OF FEDERALLY FUNDED RESEARCH

The U.S. Government may have certain rights in this invention pursuant to support by the NSF LSAMP Bridge to the Doctorate (BTD) fellowship under grant number HRD-1406755.

TECHNICAL FIELD

Embodiments of the invention are in the field of medical devices and, in particular, endovascular embolic devices.

BACKGROUND

Polyurethane shape memory polymer (SMP) foams are attractive materials for endovascular applications. SMP foams are capable of being compressed to fit inside a catheter and then actuating once exposed to body heat and water inside vasculature, achieving up to a 70-fold volume expansion. SMPs consist of net points and switching segments that are responsible for shape change. To program SMPs, the material is heated above its glass transition (Tg) temperature, and an external stress is applied to deform the material to its secondary shape. The secondary shape is then fixed by cooling the material under constant load. When exposed to a stimulus, the material returns to its primary shape.

The porous architecture of the foams provides a large surface area for rapid clotting and connective tissue infiltration. Polyurethane based SMP foams have also been shown to be biocompatible in a porcine animal model, producing a reduced inflammatory response when compared to suture materials (silk and polypropylene), cellular infiltration, and endothelialization. These materials are also highly tunable to cater to specific endovascular applications, and have been shown to achieve complete occlusion within 5 minutes.

Closure of the left atrial appendage (LAA) is a treatment option for patients suffering from atrial fibrillation to reduce their risk of stroke. Atrial fibrillation (AF) is an abnormal heart rhythm that is associated with significant morbidity and mortality. It affects roughly 6.1 million individuals in the USA, which is expected to increase to 12 million individuals by 2050. Patients suffering from AF have an irregular heart rhythm that results in a pooling of blood in the atria and formation of clots in the appendage. The formation of clots increases risk of stroke, which is the third leading cause of death in the USA. Data suggests that 15% of all strokes are attributable to AF. In the mid-1950s, it was found that the majority of clots in patients with AF were formed in the LAA.

A conventional treatment for preventing stroke in AF patients is oral anticoagulation therapy. However, oral anticoagulation therapy is not well tolerated by patients due to its interaction with other medications, potential for bleeding, and narrow therapeutic window. Given that fewer than 50% of patients with AF are considered candidates for oral anticoagulation therapy, and that the LAA is the source of 90% of atrial thrombi, LAA closure is a desirable treatment. LAA closure can be performed surgically or percutaneously with epi- or endo-cardial devices.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 1: H40 SMP foams with increasing bore diameter.
FIG. 2: Investigated H40 foams.
FIG. 4: Axial and transverse pore sizes of foam batches.
FIG. 5: Wet and dry $T_g$ temperatures for small, medium, and large pore foams.
FIG. 7: The average expansion ratios±standard deviation of H40 foams as a function of bore and pore size (N≥3).
FIG. 9: Design considerations for the development of an embodiment.
FIG. 11: Medical fibers and biotextiles used in embodiments.
FIG. 12: Comparison of investigated membrane materials.
FIGS. 13(A), (B), (C), and (D) illustrate a manufacturing process in an embodiment.
FIG. 16: Summary of embodiment composition.
FIGS. 17(A), (B), (C), (D), and (E) depict fabrication of an embodiment.
FIG. 21: Description of embodiments used in the bovine blood study.
FIG. 23: Results of submerged embodiments in bovine blood.
FIG. 24: Mean±standard deviation of particles counted.
FIG. 27 addresses mechanical properties of TPU film compositions used to fabricate SEDs.
FIGS. 28(A), (B), (C), and (D) address mechanical properties of H40 foam.
FIG. 29 includes an embodiment of a membrane encased foam coupled to a shape memory metal.

DETAILED DESCRIPTION

Figure 3A:
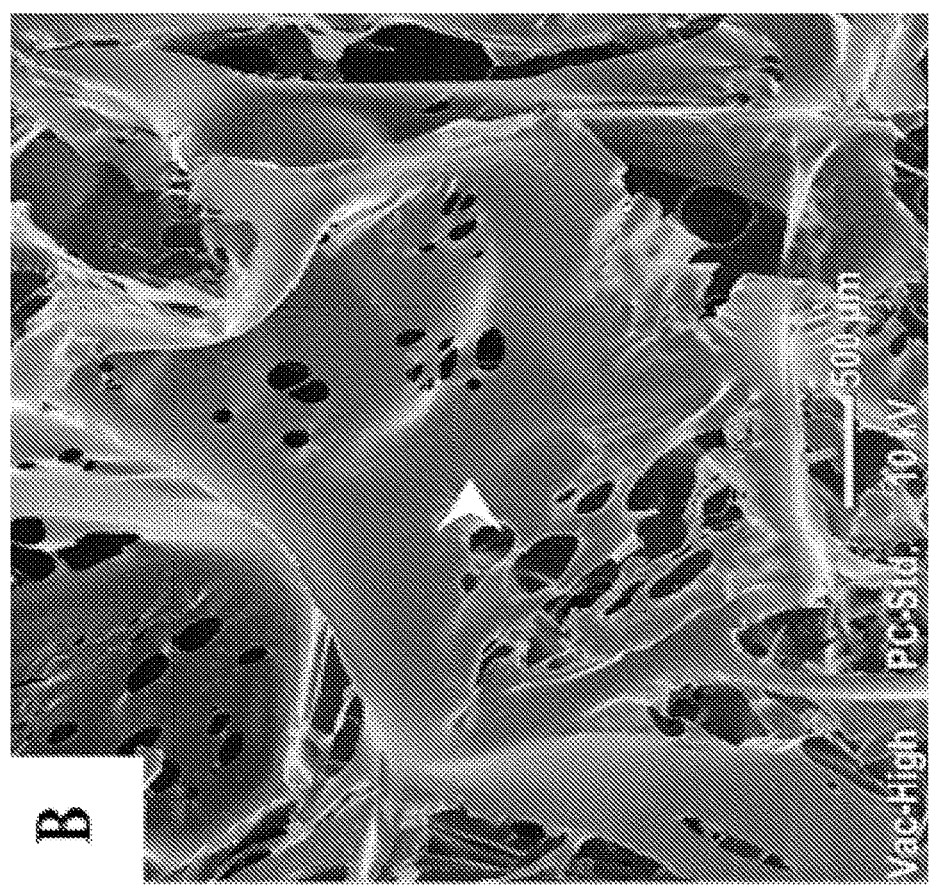
FIG. 3(A): Image of SMP foam with an open-cell pore.

Reference will now be made to the drawings wherein like structures may be provided with like suffix reference designations. In order to show the structures of various embodiments more clearly, the drawings included herein are diagrammatic representations. Thus, the actual appearance of the fabricated circuit structures, for example in a photo, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Percutaneous closure of the LAA is associated with a less invasive procedure, a faster recovery time, and reduced risk of bleeding. In general, devices for percutaneous closure are composed of a self-expanding nitinol frame with barbs, or anchors, that exclude the LAA while engaging the surrounding tissue to prevent migration. Complications from these devices include air embolism, pericardial effusions, tamponade, tissue tearing, device embolization, and stroke.

Applicant determined partial to full volumetric occlusion of the LAA cavity, as opposed to just sealing the entrance to the appendage, may improve outcomes. Embodiments described herein include an embolization device composed of SMP foam that is capable of occluding a LAA. Embodiments may include foams that integrate with hard materials, like nitinol, to improve fluoroscopic guidance and cavity sealing. A method to protect the SMP foam from hard materials will also be discussed.

Particulate Matter

As used herein, particulates are mobile undissolved particles that are unintentionally present in media. Implanted devices that are upstream of brain vasculature pose a unique and significant risk of generating particulates that can cause transient ischemic attacks or strokes. Therefore, Applicant determined procedural or device controls are needed to mitigate the risk.

Embolization devices are at risk for generating harmful particulates. To mitigate the risk and generation of device-related particulates, an embodiment provides a thin polymeric membrane that encapsulates the SMP foam and serves as a barrier and emboli protector.

Approach

Incorporation of SMP foam in a LAA closure device results in rapid clotting, endothelialization, and tissue ingrowth that biologically fixates the device within the appendage. As a result, adverse events, such as device thrombosis, device migration, and incomplete occlusion may be reduced. Current devices generally lack a volume filling occlusion member, and serve their function of preventing stroke by sealing the ostium of the LAA.

To improve volume occlusion, an embodiment includes a device comprised of SMP foam encapsulated within a membrane. The sheathed SMP occlusion device can be integrated into existing devices or be used individually to embolize vasculature in various embodiments. The encapsulated SMP foam can be attached to proximal and distal marker bands to enable fluoroscopic guidance and device delivery. The membrane functions as a filter between the SMP foam and surrounding environment to capture any foam particulates that are generated during delivery. The membrane may also aid in endothelialization of the device. Additional features include a detachment mechanism that can connect to a delivery cable. Embodiments discussed herein improve occlusion times, reduce particulate generation, and serve as an adjunct for predicate occlusion devices.

More specifically, embodiments include an SMP-based embolization device that can be integrated with hard materials, without increasing the generation of device-related emboli. An application of an embolization device comprised of SMP foam and nitinol is the closure of LAAs. With that in mind, embodiments include a sheathed embolization device (SED) for occluding a LAA and mitigating the generation of device-related emboli.

1. SMP CHARACTERIZATION

Applicant determined certain characteristics embodiments of a SMP foam should possess for use in some endovascular occlusion embodiments include: the ability to remain stored in their secondary configuration, the ability to volumetrically fill cavities upon exposure to a stimuli, positive blood and tissue interactions, and/or a tailored actuation profile. Several characterization techniques were employed to characterize the thermal properties that regulate the shape change of SMP foam, as well as the geometric architecture of SMP foams.

The characterization techniques aided in the design and development of an embolic device to occlude LAA's. An embodiment may volumetrically fill the LAA cavity in a reasonable manner, then subsequently allow rapid and stable thrombus formation within the cavity. Over the span of 90 days the exposed surfaces of the SMP foam may become endothelialized in some embodiments, forming a neointima at the ostium of the LAA. SMP foams have the ability to form discontinuous and continuous endothelial layers at 30 and 90 days. Further, cellular, connective, and granular tissue infiltration is observed within the SMP foam scaffolds, suggesting an active healing response. Herein, several SMP foam geometries are disclosed and may be delivered via various procedural techniques in order to fill a large LAA.

1.1 Materials and Methods

SMP Synthesis

Polyurethane SMP foams were synthesized following a three-step protocol. Briefly, isocyanate prepolymers composed of appropriate molar ratios of N,N,N',N'-tetrakis(2-hydroxypropyl)ethylenediamine (HPED, 99%; Sigma-Aldrich Inc., St. Louis, Mo.), triethanolamine (TEA, 98% Sigma-Aldrich Inc.), and hexamethylene diisocynate (HDI, TCI America Inc., Portland, Oreg.) were synthesized. The isocyanate prepolymer is then reacted with a hydroxyl mixture blended with the remaining molar equivalents of HPED and TEA. The hydroxyl mixture also contained catalysts (T-131 and BL-22, Air Products and Chemicals Inc., Allentown, Pa.) and deionized (DI) water. To create foams the isocyanate prepolymer and hydroxyl mixture were combined with surfactants (DC 198 and DC 5943, Air Products and Chemicals Inc.), and a physical blowing agent Enovate (Honeywell International, Inc., Morristown, N.J.) to create SMP foams.

Foam formulations are denoted as HXX, where "XX" corresponds to the ratio of HPED to TEA equivalents. Varying the ratio of HPED to TEA enables tuning of the thermo-mechanical properties of the foam. Based on previous internal investigations and inventory, a foam composition of H40 was investigated. The mechanical properties of H40 foams used herein are addressed below.

Foam Processing

Following foam synthesis, the bulk foam was cut into rectangles that were 7 cm long, 6 cm wide, and 2 cm thick using a hot wire cutter. The rectangular blocks of foam were then placed into a fixture and penetrated by an array of pins while subjected to low amplitude, high frequency perturbations. This process, coined reticulation, allows the creation of an open-cell network that allows blood and cellular infiltration throughout the foam matrix.

Cylindrical foams 3 cm in diameter were then cut from the reticulated foam rectangles using a 3D printed hole puncher. A 3 cm foam diameter was chosen to treat large LAA cavities, and approximates the size of large LAA closure devices. By approximating large LAA closure devices Applicant simulated the "worst-case" scenario for delivery and match industry standards. LAA closure devices are typically oversized by 9 to 30% relative to the maximum LAA ostium diameter; therefore a SED with a 3 cm outer diameter (OD) may occlude a LAA with an ostium of approximately 23 to 27.5 mm.

The center of the cylindrical foams were then bored out with disposable biopsy punches (Sklar Surgical Instruments, West Chester, Pa., USA) or with custom hole punchers, resulting in hollow cylinders (FIG. 1). The centers were bored out to enable delivery through smaller catheters and to maximize expansion ratios. FIG. 2 outlines the foam geometries.

After the foams were cut into their final geometry, they were cleaned to remove unreacted monomers, plasticizers, and particulates. A cleaning cycle consisting of submerging foam in 99% isopropyl alcohol (IPA, VWR, Radnor, Pa.) and rinsing with reverse osmosis (RO) water under sonication was performed. The amount of solvent used was approximately 20× the volume of foam. After cleaning, the foams were placed in aluminum trays with RO water and allowed to freeze in a −20° C. freezer for 12 h before freeze-drying in a FreeZone Freeze Dryer (Labconco, Kansas City, Mo.) for 24 hours.

Differential Scanning Calorimetry (DSC)

Each batch of foams synthesized had their dry and wet glass transition ($T_g$) temperatures characterized using a Q-200 dynamic scanning calorimeter (DSC) (TA Instruments Inc., New Castle, Del.). The dry and wet $T_g$ of the foam can help elucidate at what temperatures the foams will actuate at under dry and wet conditions. Applicant determined these temperatures have important implications in terms of storing the foam samples, and understanding the expansion kinetics when the foam is inside the body. In other words, dry and wet $T_g$ can determine whether or not the foam will expand prematurely outside the body; or if it will expand once inside the body.

Foam samples (3-10 mg; N=3) were taken from already processed foam cylinders. Samples used for dry $T_g$ analysis were hermetically sealed and packed in aluminum pans. The DSC protocol specified an initial sample cooling to −40° C. at a rate of 10° C./min, then holding it isothermally for 2 min. Following the cooling cycle, a heat ramp at a rate 10° C./min to 120° C. occurred. The cooling and heating cycle was then repeated twice; the last heating cycle was analyzed to quantify dry $T_g$ values of the foam. The $T_g$ measurement was based on the inflection point of the thermal transition curve using TA Instruments software.

Wet $T_g$ foam samples were submerged in RO water at 50° C. for 15 minutes to allow full plasticization. Samples were then removed from water, sandwiched between Kimwipes (Kimberly-Clark Professionals, Roswell, Ga.), and press dried with a mechanical press (2 tons, 30 seconds). Samples were then weighed (3-10 mg) and placed in aluminum pans with a vented lid. The DSC protocol decreased the temperature to −40° C. at 10° C./min and held it isothermally for 2 minutes. The temperature was then increased to 80° C. at 10° C./min. The wet $T_g$ measurement was based on the inflection point of the thermal transition curve using TA Instruments software.

Imaging

Foam pore sizes, strut thickness, and cell structure were analyzed by taking magnified images of thin slices of foam using a high resolution light microscope (VHX-5000, Keyence Corporation, Osaka, Japan) and a scanning electron microscope (SEM, Joel NeoScope JCM-5000, Nikon Instruments Inc., Melville, N.Y.). Transverse and axial slices of foam were prepared by cutting foam with a razor-sharp scalpel. Foam samples were mounted onto the light microscope stage and imaged at different magnifications (20× to 200×). Keyence software allowed for real-time depth composition and 2D/3D stitching of the foam samples, thus providing focused images. Additionally, length measurements of the foam were taken with Keyence software, wherein the pore diameter was taken as the maximum diameter. Ten measurements were taken to account for variation in pore sizes.

SEM samples were prepared by first thinly slicing sections from bulk foam with a razor sharp scalpel. The thin slices were then mounted onto a SEM platform with carbon-tape and placed under vacuum at room temperature overnight. The samples were then sputter coated with gold for 60 s at 20 mA using a Cressington sputter coater (Ted Pella Inc., Redding, Calif.). Samples were then placed in the SEM chamber and imaged under high vacuum at a voltage of 10 kV or 15 kV.

SMP Foam Actuation

Actuation, or expansion, studies are performed to characterize how quickly SMP foams will expand inside the body, and how large they will expand. In some embodiments, the SMP foams expand in an appropriate time that prevents premature expansion inside the delivery catheter and allows full expansion inside the body cavity.

Prior to performing the actuation studies, crimped foam samples were prepared. Processed SMP foam cylinders described in FIG. 2 were crimped over a 0.008" nitinol wire using a SC250 Stent Crimper (Machine Solutions Inc., Flagstaff, Ariz., USA). The SC250 Stent Crimper was set to a crimping pressure of 80 pounds per square inch (PSI) at 100° C. Foam samples were allowed to equilibrate to 100° C. and reach a rubbery state before crimping. Once equilibrated the SC250 Stent Crimper was closed and cooled to room temperature. The foam samples were then removed and their crimped diameters measured with calipers.

Actuation studies were conducted by loading crimped samples to a fixture, submerging in a heated water bath, and imaging at specific time points. The samples were loaded to a fixture to keep the threaded nitinol wire, and sample, taut. The water bath was heated to approximately body temperature (37.5° C.). Samples were then placed into the water bath and imaged every 30 seconds using a digital camera (PowerShot SX230 HS, Canon Inc., Tokyo, Japan) until they foams were fully expanded. The images were then analyzed with either ImageJ (NIH, Bethesda, Md.) or an interactive MATLAB program (MathWorks Inc., Natick, Mass., USA).

1.2 Results

Imaging

Figure 3B:
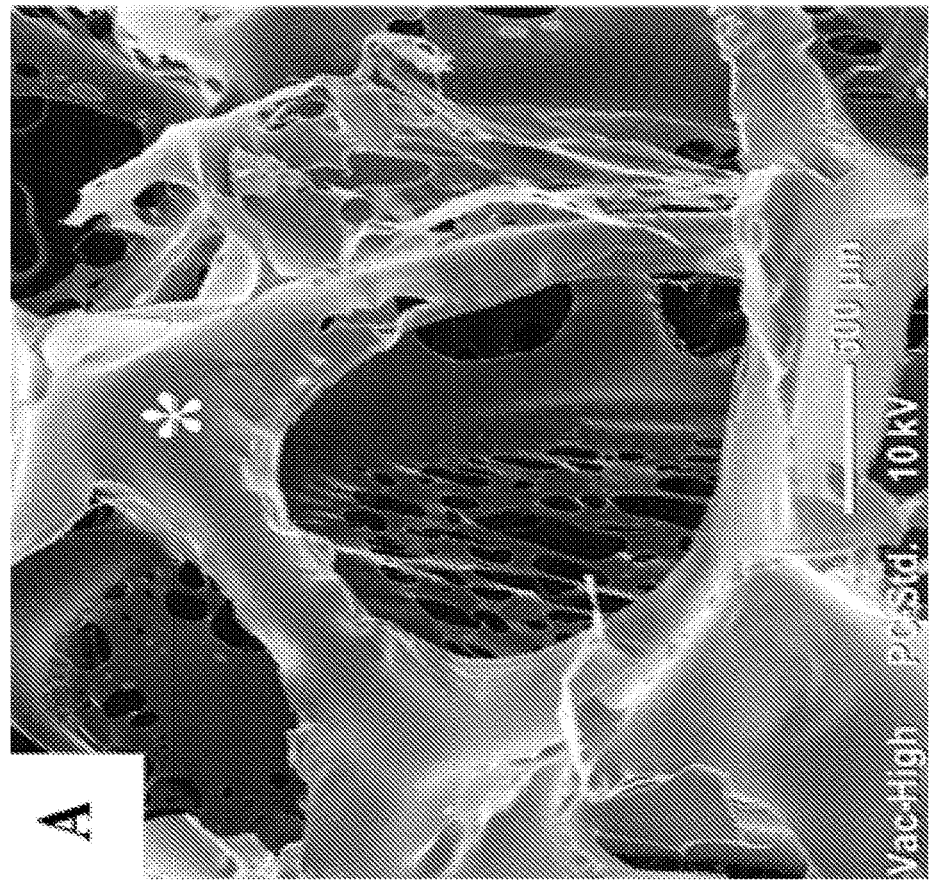
FIG. 3(B): Image of a partially close-cell pore.

Light microscopy and SEM imaging revealed foam architecture and the impact reticulation has on foam processing. Applicants imaged an open-cell foam as well as partially closed-cell and open-cell morphology foams (FIGS. 3A and 3B).

Due to the foaming process thin residual membranes are observed between struts. The membranes form a predominantly closed cell structure, and can be removed by secondary physical processes such as hydrolysis, oxidation, heat, plasma etching, or mechanical treatment. A closed cell microstructure may not be conducive for embolic materials in some embodiments as the lack of interconnected pores limit cellular infiltration during healing. Further, a closed cell microstructure may generate a large pressure gradient when deployed in the body, potentially causing the material to migrate after deployment. For these reasons mechanical reticulation was carried out, successfully resulting in a predominantly open-cell microstructure as shown in FIGS. 3A and 3B.

Mechanical reticulation did not eliminate membranes entirely, but instead resulted in pseudo-open cell structures. FIG. 3B shows a membrane that has micro-holes perforated through it. Applicant determined that for the application of occluding a LAA the lack of completely open cells is not anticipated to be a major issue. Since the LAA is a terminal cavity with no downstream vasculature the danger of device migration downstream is non-existent, therefore a pressure gradient from a closed-cell structure is a low-risk situation. Applicant determined key benefits of an open-cell microstructure for this application include rapid occlusion due to the formation of stable thrombus triggered by flow stagnation and recirculation through the interconnected foam matrix; as well as a cellular infiltration that improves the healing response. For embodiments described herein, 0.008" nitinol wires punctured the membranes to provide a more open-cell structure. Despite incomplete removal of the membranes, 0.008" punctures are large enough to allow cells to infiltrate throughout the volume of the foam matrix.

Reticulation also affects the overall physical properties of the SMP foam. Reticulated foams have a decrease in the resistance to mechanical compression. Less resistance to compression may result in tighter crimping of the foam, thus decreasing the crimped diameter of the foam. A more compressed foam is beneficial to clinicians as it enables delivery through a low-profile catheter. Reticulation results in significantly higher levels of particles when compared to a non-reticulated foam. Embodiments include an approach to mitigate particle-release due to mechanical reticulation includes the encapsulation of the foam by a filter membrane.

Pore Size

Eight foam batches were imaged in the transverse and axial directions, and were categorized as small (S), medium (M), or large (L) pore. FIG. 4 summarizes the pore sizes of each foam batch, and their respective pore classification. Based on the results in FIG. 4, foams were cut in either the axial or transverse direction to achieve a suitable pore sizes. Anisotropic pore cells were also apparent from the difference in pore size between axial and transverse slices, which is typically seen in blown foams.

Pore size is believed by Applicant to affect several key characteristics of foam performance. Mechanical analysis on several pore sizes illustrates that foams with smaller pore sizes exert a greater radial force due to increased foam density. Radial force is clinically significant as too low of a radial force poses a risk of the foam migrating, whereas a high radial force poses a risk of bursting or perforating the vessel. Fortunately, vessel rupture from high radial force is not a realistic risk of the present foam compositions considering prior testing oversized similar foams by 50% to the target vessel and showed a radial force significantly lower than the required rupture force. Device migration due to low radial force is a concern, however, in some embodiments. To mitigate the risk of the foams migrating out of the LAA a nitinol frame may anchor the foam to the vessel wall.

Pore size, and thus foam density, also affects expansion rates. Smaller pore sizes, or higher foam density, delays water from penetrating and plasticizing the foam. As a result, foam may not expand as fast when compared to larger pore foam.

Thermal Properties

DSC was used to characterize the thermal properties of the thermoset SMP foams in wet and dry environments. In particular, the transition temperature at which foams undergo shape change corresponds to the $T_g$. FIG. 5 shows that the average dry $T_g$ of all investigated foams was between 59° C. and 64° C. with a max deviation of ±2.4° C. Based on the dry $T_g$ results the foams may be stored at room temperature if the surrounding environment is dry. The wet $T_g$ was between 13 and 16° C., indicating that the foam will undergo shape change when placed into the body.

Pore size did not have a significant effect on the transition temperatures of the foam. This is expected as the foams were all of the same composition (i.e., H40). By varying the ratio of HPED to TEA in the foam formulation the transition temperatures can be precisely controlled. Applicant determined that the secondary hydroxyl group within HPED can present steric hinderance to rotational motion around the urethane linkage, and HPED can provide a higher crosslink density in comparison to TEA; thus increasing the $T_g$. Applicant showed that an H20 composition had a $T_g$ 20° C. less than the higher HPED content H60 composition.

Expansion Profiles

Characterizing the rate of expansion and final crimped diameter may be critical to the performance of an embolization device. The crimped diameter regulates what size delivery catheter is suitable; typically, a lower-profile delivery catheter is desired as it can access more vasculature. The rate of expansion of SMP foam determines whether premature or delayed expansion will affect procedural outcomes. Premature expansion can cause the device to occlude the catheter, thus preventing deployment. Incomplete, or delayed expansion can result in incomplete occlusion of the vasculature, prolonged procedural times, or migration of the device.

Figure 6:
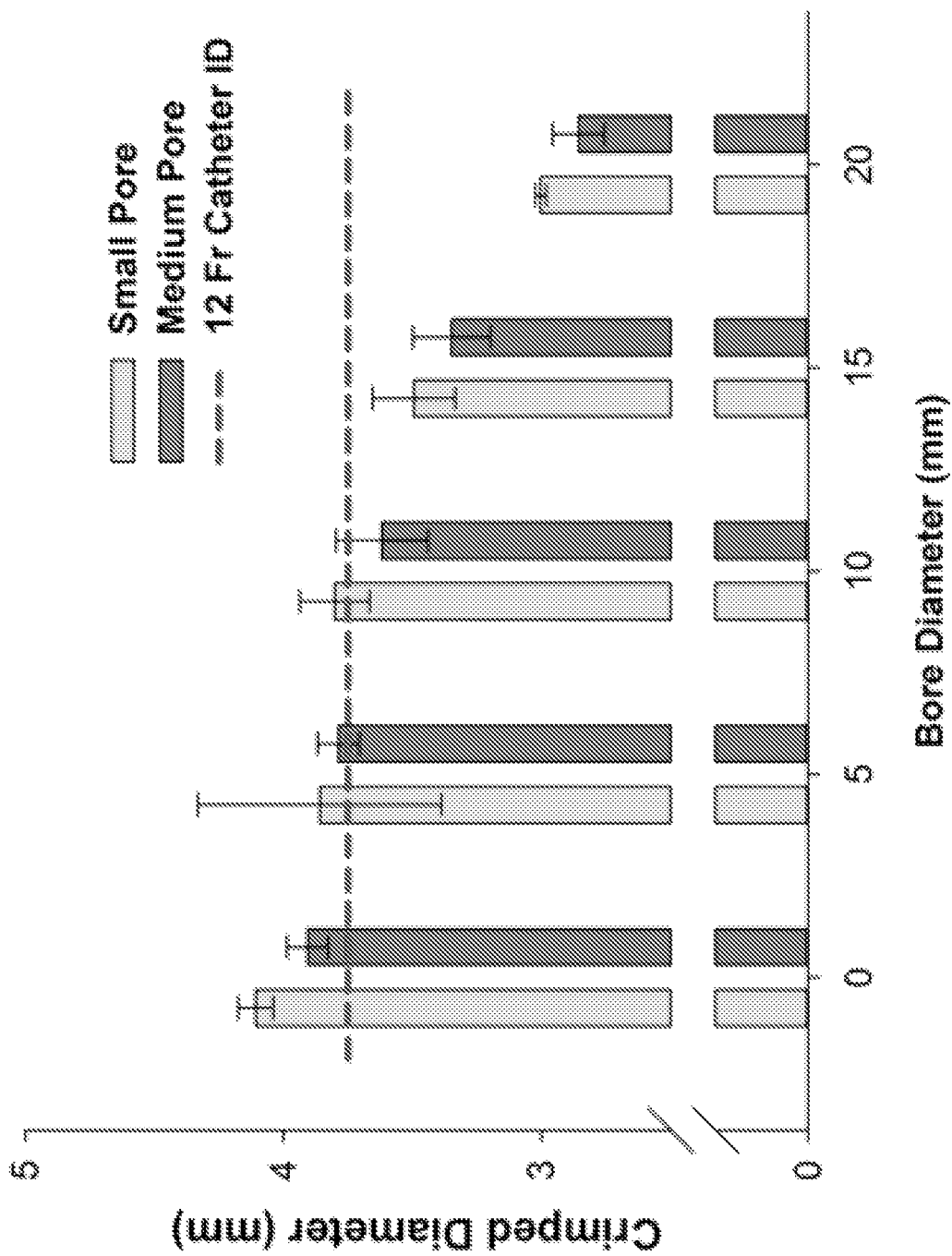
FIG. 6: Final crimped diameter as a function of pore and bore diameter.

FIG. 6 shows the final crimped diameter of a foam embodiment as a function of bore diameter and pore size. Pore and bore size both had an effect on the final crimped diameter. In general, a trend depicting a decrease in crimped diameter as bore and pore size increased was observed. As bore and pore size increased the foam density decreased, thus allowing the foam to be crimped to smaller diameters.

A two-way analysis of variance (ANOVA) with Tuley post-hoc multiple comparison was conducted to examine the effect of pore size and bore size on crimped diameter of SMP foam. Main effect analysis showed increasing pore and bore size significantly decreased crimped diameter. However, there was no significant interaction between pore and bore size. Tukey pairwise multiple comparison showed a significant difference between the majority of bore sizes when pore size was held constant. There was no significant difference between pore sizes, however. Two-way ANOVA was performed using Graphpad Prism 7 (Graphpad Software, Inc, La Jolla, Calif.).

FIG. 7 shows increasing bore and pore sizes increase the expansion ratio of foams, wherein the expansion ratio is defined as:

$$\text{Expansion Ratio} = \frac{30 \text{ mm}}{\text{Crimped Diameter (mm)}}$$

A max expansion ratio greater than 10 and a 61-fold volumetric expansion was recorded.

Figure 8:
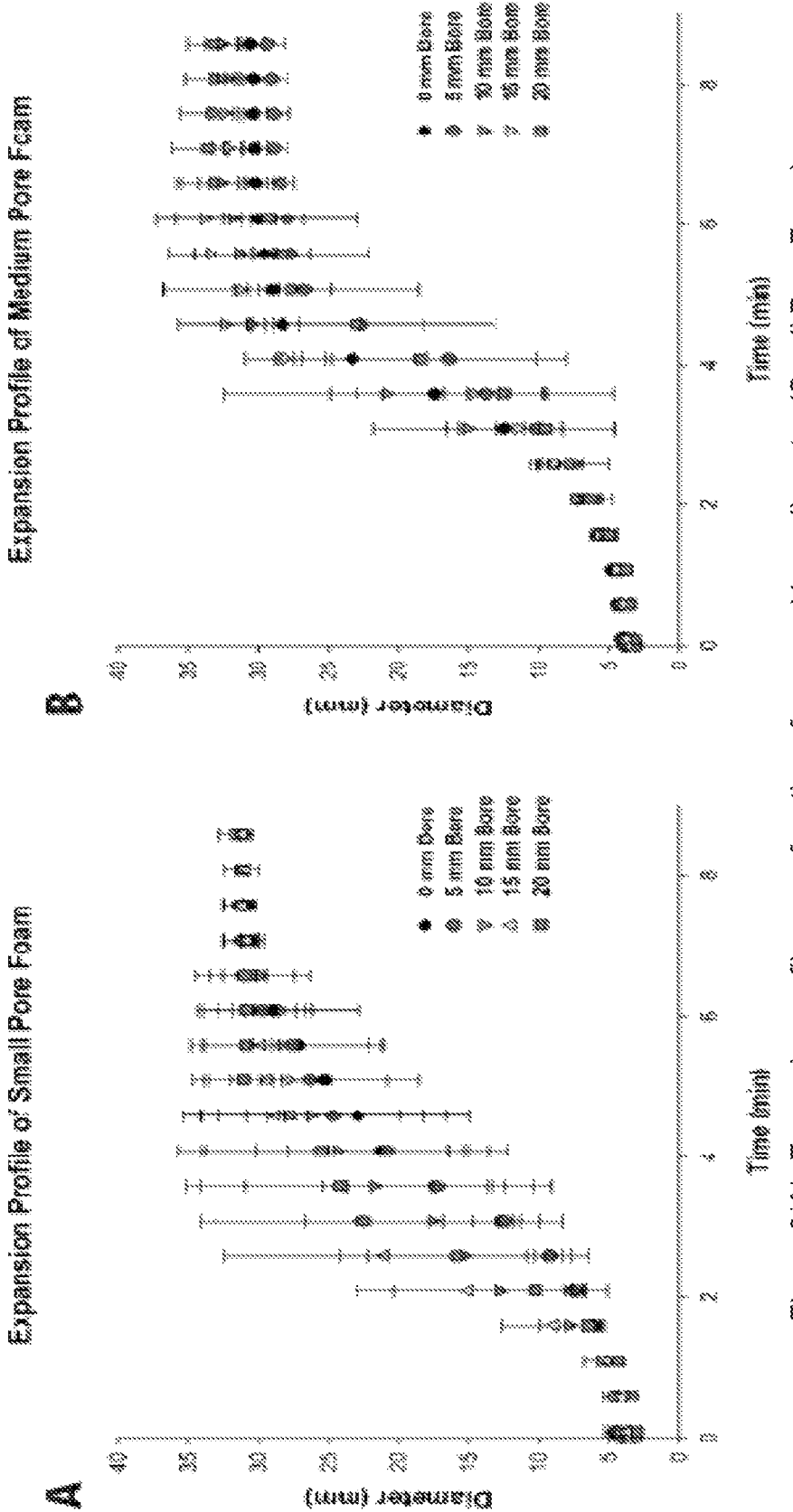
FIGS. 8(A) and 8(B): Expansion profiles as a function of pore and bore diameter.

The rate of expansion of SMP foams as a function of pore and bore diameter is shown in FIGS. 8(A) and 8(B). Most foams were able to expand to their original diameter in body-temperature water in under 10 minutes. To identify any trends in the data an index was selected for each data set and compared. The index was taken as the time it took the foam to expand to half its expanded diameter. No statistical or qualitative trend was observed.

Possible explanations for the lack of observable trends include: compromised mechanical properties due to boring of the foam that affected shape memory, irregular crimping, temperature fluctuations, or image analysis error.

A potential complication for passively-actuated embolization devices is premature expansion in the delivery catheter. To compound the risk, it is common practice to flush the delivery catheter containing the embolization device with saline to purge air and prevent air embolisms. To mitigate premature expansion of the foam the $T_g$ may be tailored appropriately. Furthermore, the encapsulation of the SMP foam within a membrane or nitinol frame may be able to contain the foam enough to allow the clinician to deliver the device.

2. DESIGN AND FABRICATION OF A SHEATHED EMBOLIZATION DEVICE

While SMP foam is a promising material for embolization devices, there exists a risk of unintended ischemia due to foam particulates entering the blood stream as emboli. Applicant determined this risk is compounded if SMP foam is in contact with nitinol mesh, wire, or other hard materials that can mechanically shear chunks of the low-density foam. Fabrication of a stand-alone device comprised of SMP foam and an emboli-capturing membrane may prevent foam based emboli from entering the bloodstream, and expand the commercial and clinical utility of SMP foams. In an embodiment, a successfully sheathed embolization device (SED) comprised of SMP foam is integrated with metals or predicate devices to improve the current standard of care for embolization procedures.

Additional concerns for developing a stand-alone SED include the mechanism of delivery and deployment, as well as imaging under fluoroscopy. Embodiments may be secured to a delivery cable and deployed by unscrewing the delivery cable. These devices may come pre-loaded inside a delivery system and may be deployed by holding the delivery cable fixed while slowly withdrawing the delivery catheter; as opposed to pushing the device. Fluoroscopic imaging is critical to proper device placement in some embodiments, and is achieved via marker bands on the delivery system (i.e. access sheaths and delivery catheters) and from the inherent radiopacity of the nitinol that makes up the bulk of LAAC devices.

As addressed below, a SED utilizing SMP foam as the main embolic material and a thin encapsulating membrane to provide emboli protection has been developed. The SED prototype also incorporates a delivery mechanism that allows for fluoroscopic imaging to aid in device positioning. Within this chapter the material and design rationale will be provided, as well as the details for fabricating the SED. Lastly, components of the SED will be characterized to provide justification for their use.

2.1 Design Considerations

Designing a SED that takes into consideration the clinical utility, performance, safety, and manufacturing concerns can improve the quality of the final device. Design criteria and requirements for some embodiments are specified in FIG. 9.

2.2 Device Fabrication

Summary of Device Design and Fabrication

Figure 10:
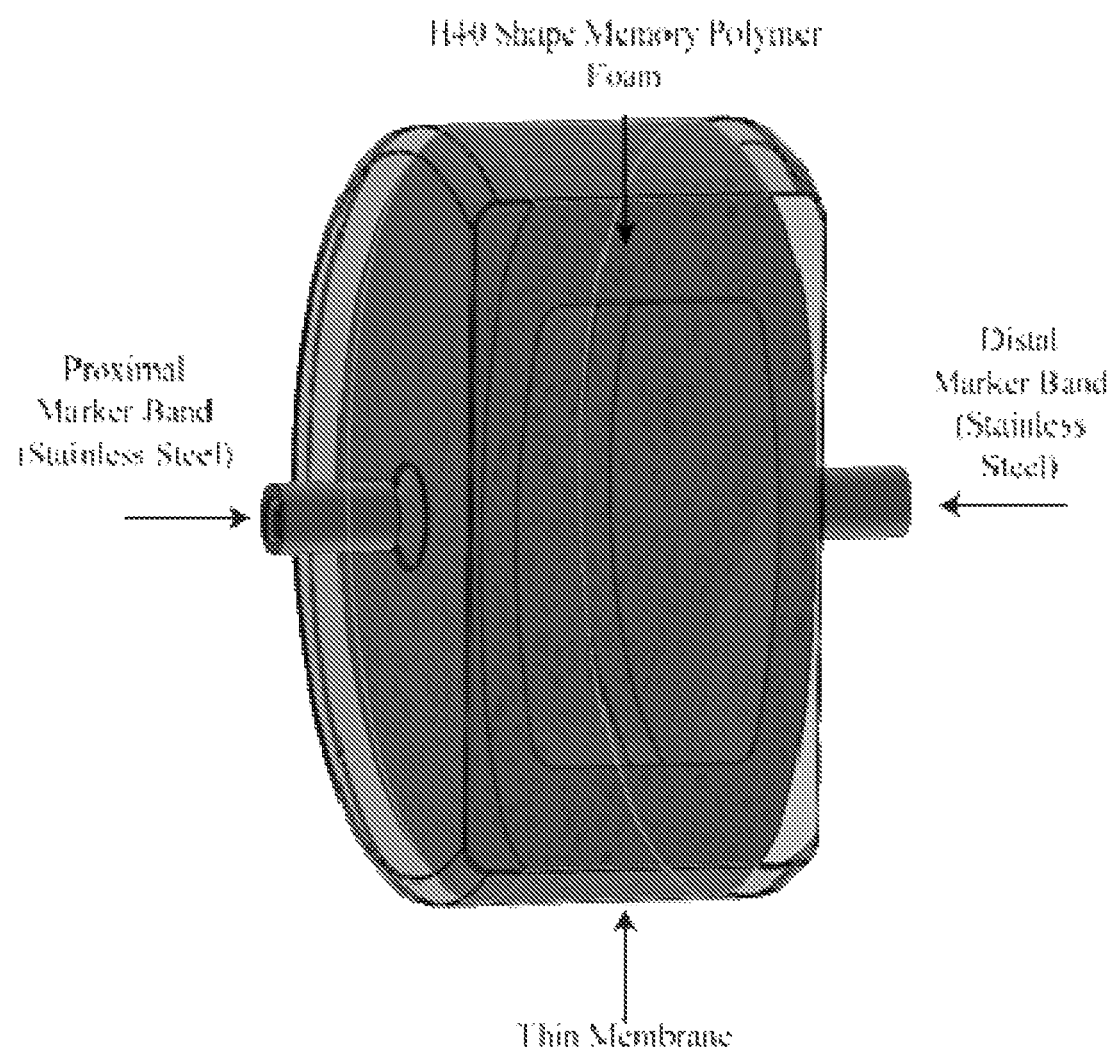
FIG. 10: Schematic depiction of an embodiment.
Figure 14:
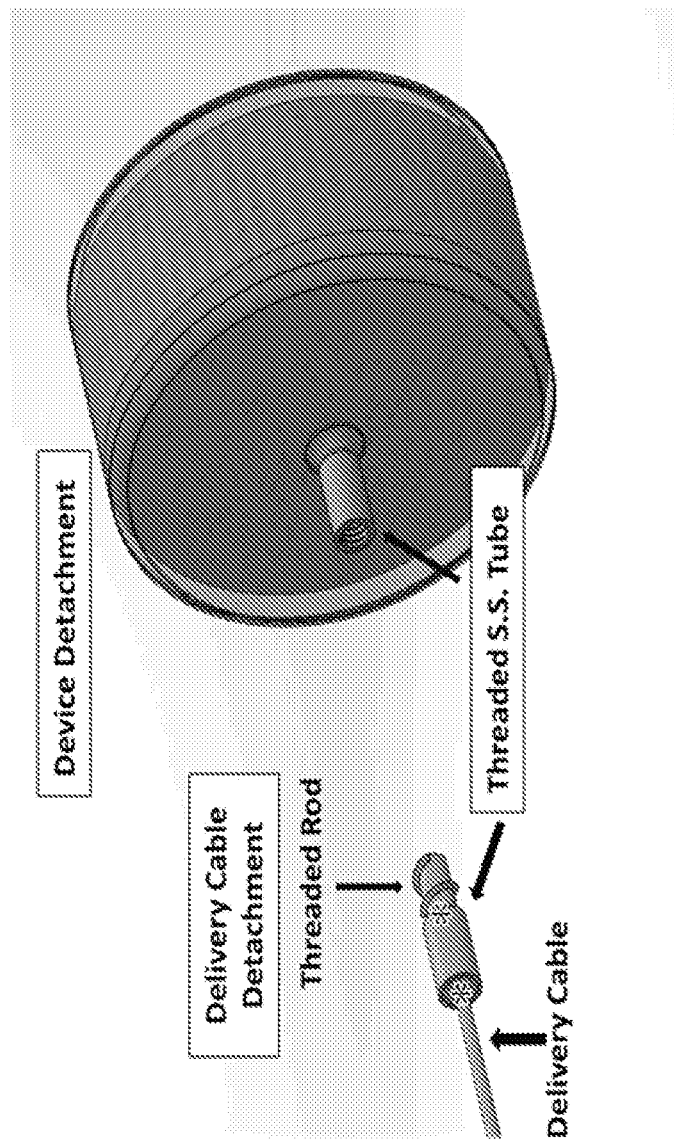
FIG. 14 depicts delivery detachment components in an embodiment.

An embodiment consisting of a SMP foam occlusion member, emboli-capturing membrane, and delivery system is shown in FIG. 10 and FIG. 14. The overall device geometry is a cylinder that is roughly 2 cm long and 3 cm in diameter in order to occlude a large LAA. In some embodiments a membrane fully encapsulates the SMP foam to capture as much foam particulates as possible. The ends of the device have marker bands to aid in device imaging, considering SMP foams not loaded with radiopaque filler have limited radiopacity. Lastly, a simple screw detachment mechanism allows the clinician to deploy the device once positioned.

Membrane Selection

Several membranes were investigated for their use in developing a SED. Materials used in various embodiments include polytetrafluoroethylene (PTFE), polyethylene terephthalate (PET), and polyurethane (PU) (FIG. 11).

Ultimately, thermoplastic polyurethane (TPU) films were chosen for some embodiments to serve as the membrane to protect SMP foam from shear forces while filtering emboli in some embodiments. FIG. 12 shows a comparison between the investigated materials. Common issues with the membrane materials included: material thickness, lack of elasticity, and the difficulty to process the material into cylinders or other geometries.

Thermoforming

In an embodiment membranes take the form of the body-cavity they are deployed in. Should membranes not be formed properly, and take on a non-ideal geometry, the SED may not expand properly to fully occlude the body-cavity. Thermoforming was considered as a method to shape and process plastic membranes. Stock membrane materials were typically delivered in a roll or as flat sheets, and needed to be processed to a shape that can house foam. Thermoforming is a secondary forming process that allows users to shape plastic in a softened, but still solid, thermoplastic state; unlike primary forming processes that occurs when the thermoplastic is a melt state. Mechanical thermoforming typically involves clamping the plastic film in a positive or negative mold, then heating the plastic above its $T_g$ or near its melting point depending if its amorphous or semi-crystalline, respectively. After the plastic is deformed or stretched over the mold it is cooled below its softening range to freeze its three-dimensional shape.

A fixture consisting of female mold and male former was designed in SolidWorks (Dassaut Systemes, Waltham, Mass.) that would shape the plastic membranes into a closed-end cylinder geometry (FIG. 13). An aluminum fixture was machined via CNC according to the design. Membranes were wrapped around the male former, placed into the female mold, clamped, and then placed into a furnace.

Depending on the thermal properties of the membrane material, the membrane was shaped into a closed-end cylinder similar to a tea-bag, and the excess material trimmed off.

Heat Sealing

Heat sealing was the method to seal the membrane of the SED in some embodiments. Two heat sealing methods were investigated. The first method consisted of using a solder iron that was heated to the membranes melting point, then applying a constant force along the areas to be sealed. However, this method was extremely unreliable as the contact force and temperature were difficult to control. The second method was to place the membrane into a fixture, clamp the sealing areas, and place the membrane into a furnace. This was achieved by wrapping the membrane around the foam and then carefully placing it into the fixture shown in FIG. 13(B). The clamped fixture was then placed into a furnace for a set time and temperature, removed, and allowed to cool back to room temperature. The seams of the membrane that were clamped were sealed together, while the rest of the membrane and foam were not thermally damaged. The result was a fully encapsulated foam. Excess membrane material was trimmed with scissors or laser.

Membrane Pore Creation

A Gravograph LS100 40 W $CO_2$ laser (Gravotech Inc., Duluth, Ga.) was used to cut pores into membrane materials. To do this, computer-aided design (CAD) software was used to make a 2-D pattern of pores and then exported to the laser-cutter software. The power and speed settings were set to 1% and 100%, respectively, for TPU films. The resolution was set to 1200 DPI.

Detachment Mechanism and Marker Bands

A simple detachment mechanism serves to deploy, reposition, and release the device from a delivery catheter. A simple threaded release system was fabricated (FIG. 14). Stainless steel (SS) was used to fabricate the detachment system due to affordability, availability, and its radiopaque properties. SS is a radiopaque material, allowing it to be imaged during interventional procedures. Placement of the SS tubes on the ends of the SED serve as marker bands for the clinician to position the device properly.

SS tubes (0.115-0.125" OD) were internally threaded (#4-40 or #0-80). These SS tubes were then epoxied to the ends of the SED to serve as marker bands, as well as to interface with the delivery cable. The delivery cable consisted of a torque cable that had a SS tube laser welded onto its distal end using an iWeld 990 (LaserStar, Riverside, R.I.). Filler wire and/or SS spacers were used to achieve a stable weld between the delivery cable and SS tube. A threaded SS rod was laser-welded at the distal end of the delivery cable/SS tube assembly, and interfaced with the SS marker bands on the SED. By simply twisting the delivery cable at the proximal end, a clinician may release the SED.

2.3 Device Characterization

Final Device Composition and Fabrication

Figure 15:
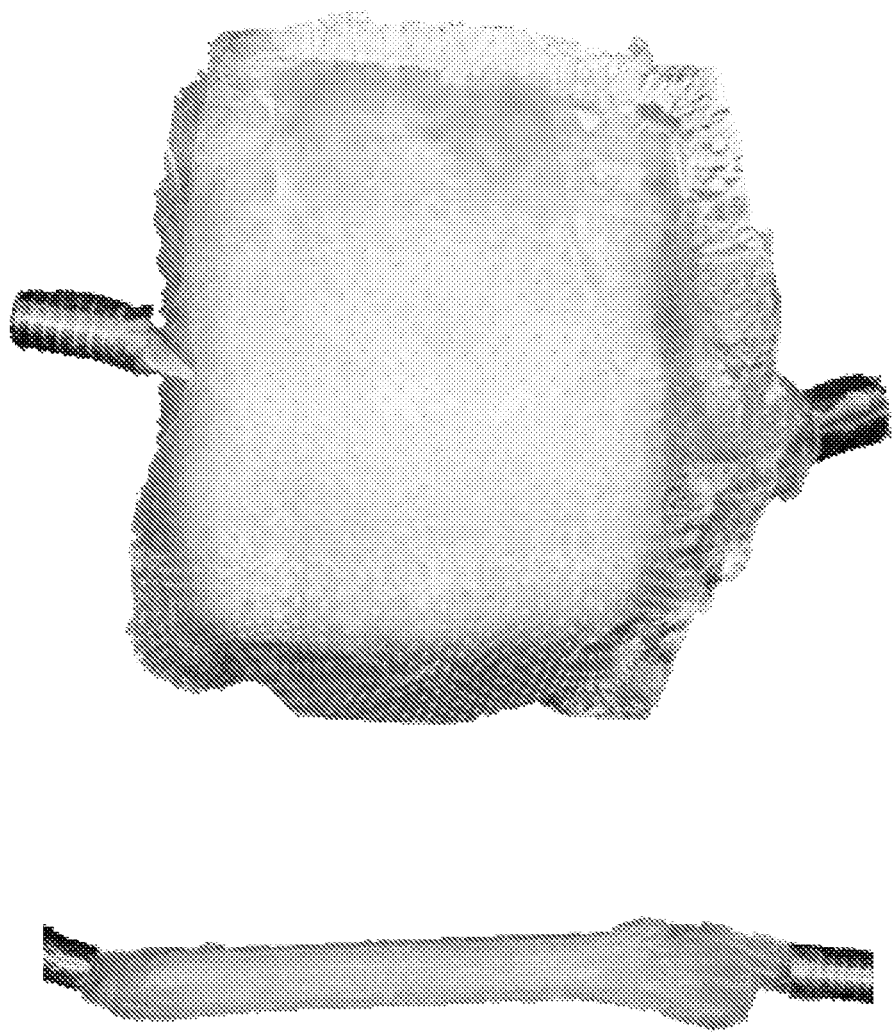
FIG. 15 depicts crimped and expanded embodiments.

The final device structure and composition for an embodiment are summarized in FIGS. 15 and 16. The steps of an embodiment to fabricate and assemble a SED are shown in FIG. 17. Briefly, a thin thermoplastic film is wrapped around a foam. The wrapped foam is then placed into an aluminum fixture. The aluminum fixture is then clamped together and placed into a furnace that is near the melting point of the film. While in the furnace, the film edges are heat sealed together. The fixture is then removed from the furnace and allowed to cool to room temperature. The fixture is then opened and the excess film is then trimmed or removed by laser. The wrapped foam is then removed and the ends are crimped. SS marker bands are then placed over the crimped ends and epoxied.

Membrane Characterization

Thermoplastic polyurethane (TPU) films (AU25, EU28, and EU29; SWM International Inc., Alpharetta, Ga.) were chosen as membrane materials to encapsulate the SMP foam in various embodiments. These materials demonstrated the ability to undergo compression and expansion alongside the SMP foam. Furthermore, improved crimped diameters were achieved due to the material's thickness and elasticity. Within this section, the morphology, thermal, and chemical properties of the TPU films were investigated. Other properties of the TPU film can be found below.

TPU film surfaces were imaged as received with SEM. A monolithic surface, as described by the manufacturer, with textured regions was observed. The textured regions, some of which appear to have pores, are most likely a result of rough handling. Despite being non-porous and a water barrier, the TPU films are breathable since they allow transmission of water vapor and have applications as wound dressings. TPU films were laser-cut to create pores, as passage of blood and cells is critical to the performance of this application.

Figure 18:
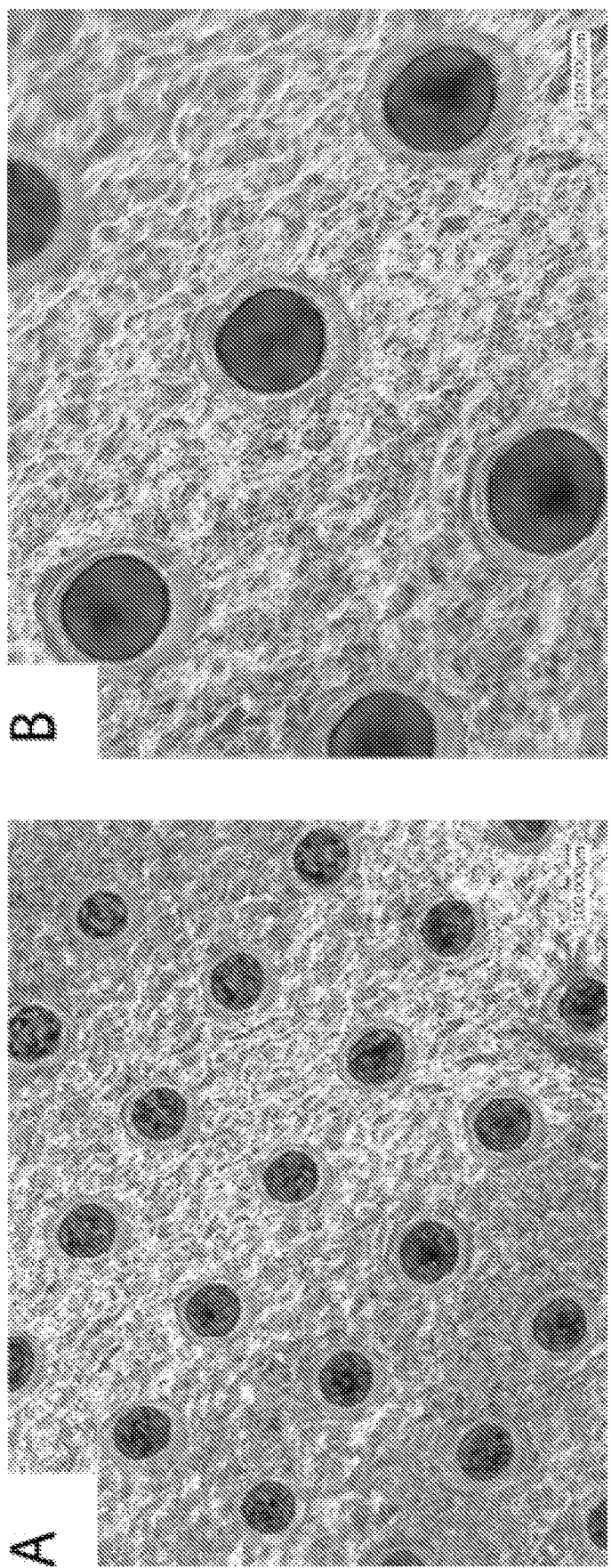
FIGS. 18(A) and (B): Images of laser created pores in TPU film.
Figure 19:
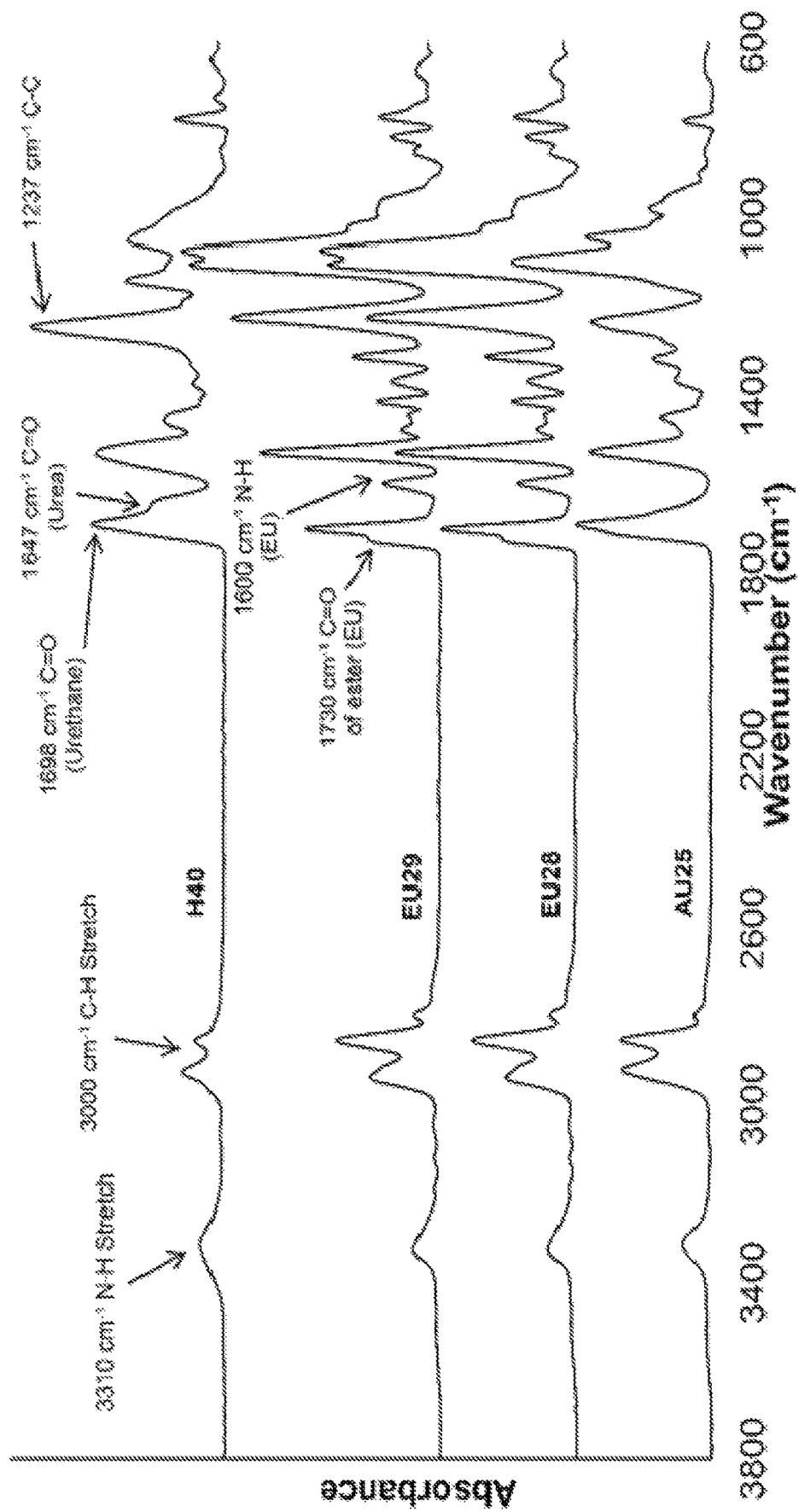
FIG. 19: ATR FTIR spectra of H40 neat films and TPU films.

Smooth concentric pores with a diameter of 261±21 µm were created with a CO2 laser (FIG. 18). Evidence of laser-induced melting was observed along the pore edges. The pores are large enough to allow blood and cellular infiltrations, while being able to capture macro particulates. The theoretical porosity of the membrane was 10.54%, and was calculated by the following equation: $Porosity = Volume_{pore}/Volume_{film}$ ATR-FTIR was performed on the TPU films as received and neat H40 samples (FIG. 19). The H40 neat samples refer to a non-blown, non-porous plastic that is compositionally identical to the H40 foams. ATR FTIR spectra were obtained using a Bruker ALPHA Infrared Spectrometer (Bruker, Billerica, Mass.) with a diamond ATR crystal and analyzed with OPUS software (Bruker, Billerica, Mass.). Thirty-two background scans of the empty chamber were taken followed by sixty-four sample scans in absorption mode at a resolution of 4 $cm^{-1}$.

ATR FTIR confirmed the presence of urethane peaks at 1689 $cm^1$ for the H40 neat film, as well as the TPU films. A strong C=O peak was observed for all plastics and suggests hydrogen bonded urethane, which is characteristics of polyurethane polymers. A urea shoulder at ≈1647 $cm^1$ was present in the H40 composition due to the reaction of isocyanates with water during synthesis. A urea shoulder is expected in H40 foams as water is the chemical blowing agent used in traditional polyurethane foaming. EU28 and EU29 TPU films had a shoulder at ≈1730 $cm^{-1}$ due to the presence of polyesters. Polyester polyurethanes have been reported to undergo rapid hydrolysis when implanted into the body, whereas polyether polyurethanes degrade via oxidation. A membrane that degrades into non-toxic byproducts following endothelialization may be used in some embodiments. AU25 TPU films lacked a 1730 $cm^{-1}$ shoulder and is a polyether polyurethane.

Figure 20:
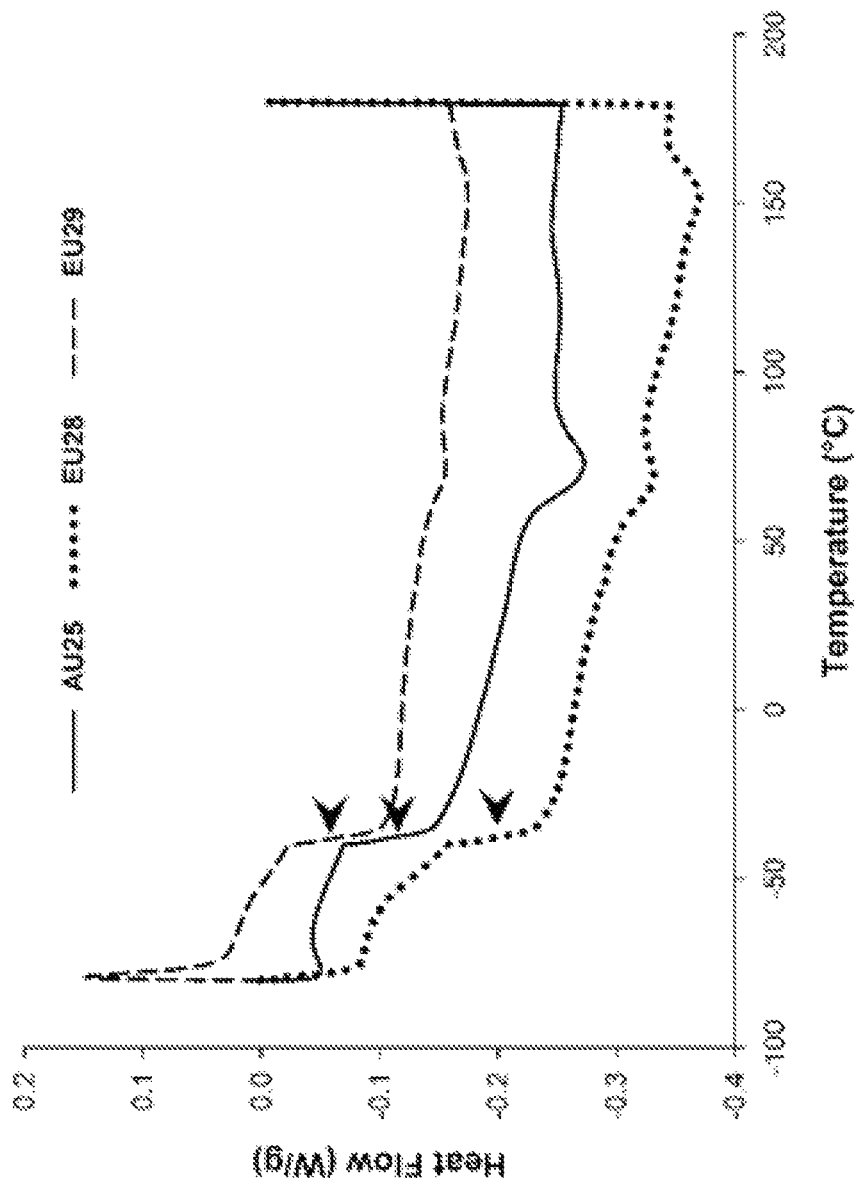
FIG. 20: DSC thermograms showing a first heating cycle.

FIG. 20 shows DSC thermograms of the films. TPU samples (3-10 mg; N=1) received were hermetically sealed in aluminum pans. The DSC protocol specified an initial sample cooling to −80° C. at a rate of 10° C./min, then holding it isothermally for 2 min. After the initial cooling, a heat ramp at a rate 10° C./min to 180° C. proceeded and the sample was then cooled back to −80° C. at the same rate.

This cycle was repeated twice. $T_g$ results did not change between cycles; but suspected melting points were erased on the following the first cycle.

Since the $T_g$ of the TPU films is below freezing (−35 to −38° C.), these materials are in their rubbery state under in-vivo conditions. Due to their extremely low $T_g$ temperatures, these films are not able to be thermoformed and do not hold a fixed shape at room or body temperature. As a result, these materials need to be expanded either by SMP foam, nitinol, or balloons in vivo. In an embodiment the TPU films are soft and flexible enough to be expanded by SMP foam. Another drawback of the thermal properties of these TPU films is that they do not hold their crimped geometry very well. In other words, once these TPU films are crimped over SMP foam they sometimes relax; potentially clogging up the delivery catheter. Thus, in other embodiments other materials may be used to form the membrane. Such materials include, for example, thermoplastic membranes with $T_g$ above 37 degrees C. (or above 30, 32, 34, 36, 39, 41 degrees C.), SMP foam membranes with a $T_g$ above 37 (or above 30, 32, 34, 36, 39, 41 degrees C.). For SMP foam membranes the membrane may include a different $T_g$ from that of the main embolic foam. For example, the SMP foam membrane may have a $T_g$ lower than the embolic foam. For example, the SMP foam membrane may have a $T_g$ higher than the embolic foam. The SMP foam membrane may have the same material composition as that of the embolic foam or may have a different material composition.

For example, to make the membrane tougher than the embolic foam in an embodiment the membrane may include an aromatic polymer while the embolic foam includes an aliphatic polymer. For example, the membrane may be tougher than the embolic foam even though the membrane and embolic foam include the same composition. For instance, the membrane may include a "skin" that naturally forms on the surface of the embolic foam as the embolic foam cures (similar to a crust that forms on a loaf of bread). For manufacturing of such a skin, the foam could be manufactured in the final geometry of the finished device to utilize this skin.

Other embodiments may include a membrane made from Dacron, PTFE, ePTFE, polyurethante, parylene, polyethylene, polypropylene, fabric, mesh, suture, and the like.

In an embodiment a membrane has a $T_g$ at, or near body temperature. This allows the membrane to retain its crimped geometry under storage conditions (i.e., room temperature with low humidity), while being able to expand under in-vivo conditions.

Delivery System

A torque cable was screwed into the marker bands of the SED. SS threaded rods and tubes were welded to the torque cable to enable screw detachment. Two screws (#0-80 and #4-40) were used to detach devices. The smaller screw, #0-80, performed better since it required less effort to detach the device. Occasionally, difficulty was noted when detaching the device. This can be attributed to poor laser-welds, improper threading, improper device placement, and a damaged torque cable.

3. TESTING OF A SHEATHED EMBOLIZATION DEVICE 3.1 Materials and Methods
SED Expansion SEDs were fabricated from medium pore SMP foams and encapsulated with TPU films. The devices were threaded over 0.008" nitinol wire. The devices were crimped in a SC250 Stent Crimper that had a crimping pressure of 80 PSI at 80° C. The SEDs did not have a porous membrane and did not have SS marker bands epoxied to their ends. The crimped diameters of the SEDs were then recorded after 24 hours with calipers.

Bovine Blood Interaction

Bovine blood was acquired from the Rosenthal Meat Science and Technology Center (Texas A&M University, College Station, Tex.) as part of a tissue share program. The blood used herein was collected from animals euthanized for purposes unrelated to this research. The blood was citrated in a 3.2% sodium citrate solution to prevent clotting, and stored at 4° C. until use.

Several SEDs were prepared to investigate how bovine blood affects their performance. FIG. 21 summarizes the SEDs used herein. The SMP foams used in all SEDs were non-cleaned, non-reticulated H40 foams. No marker bands were attached to the ends of the SEDs. Each SED was crimped and their dry weight recorded prior to the studies. Polypropylene containers were rinsed with PBS (0.1 M; 7.4 pH) and filled with 50 mL of bovine blood. The containers were then placed into a water bath to reach a temperature of 37.5° C.±0.5° C.

Activated blood was used for some samples. To activate the blood 105 µL of 0.1 M $CaCl_2$ was added to every mL of bovine blood to achieve an activated clotting time (ACT) of 120-180 s. ACT was checked by adding 2 mL of blood into kaolin-activated test vials and inserting the vials into a Hemochron® 401 (International Technidyne Corporation, Edison, N.J., USA).

SEDs were rinsed in PBS immediately prior to incubation in the containers containing blood. SEDs were submerged in citrated blood for 1 hour, and 30 minutes in activated blood. The SEDs were then removed, rinsed gently with PBS to wash away non-adherent thrombus, imaged, and dried overnight in a 50° C. oven. A control foam was placed in the oven alongside the clotted devices to ensure the devices were thoroughly dried. Once dried the SEDs were weighed to quantify the mass of clot/blood on the device. Devices were then imaged again, and prepared for SEM.

Delivery into an Anatomical Model

An anatomical model based on computed tomographic (CT) images of a human LAA was fabricated to test the SEDs. CT image data of a human heart was acquired through OsiriX image library. The left atrium and LAA were then isolated utilizing image thresholding tools on the 3D Slicer platform developed by NIH. A surface mesh of the model was then created and further processed with MeshLab software. The surface mesh was verified to ensure it was watertight and had a minimum wall thickness to enable 3D printing.

The isolated left atrium and LAA mesh was then 3D printed. The 3D printed model was then vapor polished with acetone. The 3D printed model was then placed into a box with smooth walls, and had polydimethylsiloxane (PDMS) casted around it. The PDMS was allowed to cure in a pressure chamber overnight, followed by a final cure in an oven set at 50° C. for an hour. The mold was then placed into a heated base bath to dissolve the printed material from the PDMS cast. The final result was a PDMS model in the shape of the desired vessel geometry.

SEDs were pre-loaded in PTFE tubes and were delivered into anatomic models under minimal flow at body temperature. Devices were deployed in a similar manner described above. Once the devices were deployed and fully actuated the ability to recapture them was investigated. Additionally, the device detachment was investigated by unscrewing the delivery cable from the SEDs.

Device-Ostium Apposition

Fully actuated devices deployed within the anatomical models were imaged to quantify any gaps between the device and appendage ostium. Briefly, the occluded models were positioned so the device and ostium were perpendicular to the camera's lens. Images were taken of the occluded model, along with a scale. The cross-sectional areas of the ostium and device were then measured with ImageJ. The device-ostium apposition was then quantified by taking the ratio of the ostium and device cross-sectional areas.

Particulate Quantification

Particle counting by light microscopy was performed to quantify the particles generated by SMP foam, SEDs with a porous membrane, and SEDs with a non-porous membrane (N=2). Mechanically-reticulated, non-cleaned SMP foams (30 mm OD; 20 mm length) were used as samples, and to fabricate SEDs. To improve visualization of the particles, the foam was dyed. The particle counting protocol used herein was adapted from the USP 788 microscopic particle count test.

Briefly, samples were crimped and then placed into clean glassware containing 100 mL of particle-free water. The samples were then placed into a water bath set to 37° C. for an hour under sonication to actuate the devices. The containers were then removed, inverted 20 times, and the contents passed through a cellulose filter under vacuum. The filter holder was then rinsed with 10 mL of particle-free water to re-suspend any particles adhering to the filter holder wall. Once the filter was free of water, the vacuum was stopped and the filter was carefully removed and placed onto a clean glass slide for further analysis.

Once the filter was dried, the filter was placed under a Keyence light microscope at a 100× magnification and examined. To count the particles, the Keyence systems "auto-measurement" software was used. The majority of the filter was analyzed by systematically moving the filter. Some filters were then analyzed under SEM by allowing them to dry at 80° C. overnight, and sputter coating the surface of the filter with gold.

Results were compared to the acceptance criteria specified by USP 788 for small-volume (<100 mL) injections. USP 788 identifies different acceptance criteria depending on the method of particle counting (e.g. light obscuration method vs microscopic particle count test).

To ensure the test environment did contribute significant amounts of particulate matter samples consisting of particle-free water were counted. If the particle count is greater than the specified limits then the test environment is not suitable for particulate analysis.

3.2 Results

SED Expansion

SEDs were capable of being crimped to fit within a 12 Fr catheter (ID≤3.75 mm). By encapsulating the SMP foam within a TPU film the crimped diameter was increased, on average, by 0.42±0.07 mm. The effect of bore size on crimped diameter is shown in FIG. 22.

Figure 22:
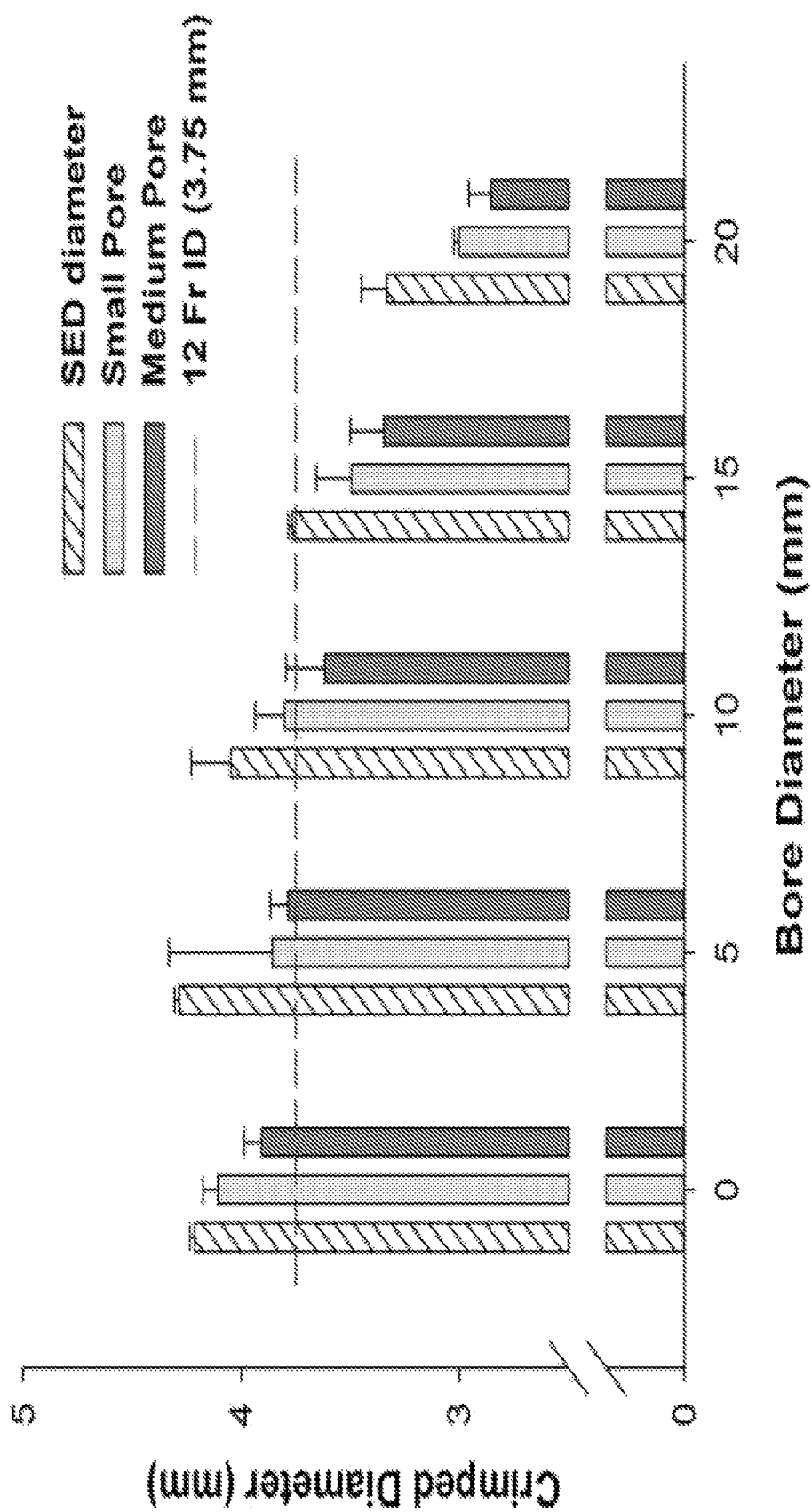
FIG. 22: Crimped diameter of embodiments as a function of bore diameter.

The crimped diameter reported in FIG. 22 includes the 0.008" nitinol wire threaded through the device, which was done to perform actuation studies. In an embodiment the crimped diameter decreases by 0.008" (0.20 mm) when fabricated without the nitinol wire. Actuation studies were performed on non-porous devices with an unestablished fabrication protocol, and therefore was not included herein. However, qualitative visual inspection of SEDs actuating during in-vitro studies resulted in full expansion in under 8 minutes.

Device-Blood Interaction

Gravimetric analysis and qualitative images show SEDs were able to form clots and/or adsorb blood components. All devices were able to fully actuate when submerged in bovine blood, with the exception of a SED with a non-porous membrane that was submerged in activated bovine blood. The non-porous SED submerged in activated blood did not fully actuate because blood was not able to penetrate the device and depress the $T_g$ before becoming clotted.

Thrombus formed in the gaps between SMP foam and the membrane. This is beneficial as the additional thrombus may improve volumetric filling of the target vessel and prevent SMP particles from entering circulation. No blood clots formed on devices submerged in citrated blood. However, citrated blood was adsorbed throughout the entirety of the devices. FIG. 23 shows a major difference between the mass of clot formed on porous and non-porous SEDs. The mass of a control foam was recorded prior to submerging it in water and after drying it alongside clotted foams to verify all moisture was removed.

SEM analysis revealed signs of thrombus-related events on SMP foam and TPU films that were submerged in activated bovine blood. On both SMP foam and TPU film surfaces droplet-like formations appeared. These droplet-like formations are thought to be related to the oven-drying procedure. Additionally, what appears to be platelet clusters intertwined with fibrin is observed on the surfaces of both SMP foam and TPU film.

Device Delivery

More than half of all the devices were delivered without complications and expanded to fill the ostium of the appendage in <8 minutes. The majority of the complications were a result of insufficient radial force from the device to keep them fixed in the anatomic model. As a result, the device rotated with the detachment mechanism during deployment. Transitioning from a #4-40 to #0-80 screw improved the results, but ultimately some embodiments may use fixation mechanisms to be fixed in the anatomy. This can be achieved by incorporating nitinol, SMP, coils, hooks, barbs, or screws to the device to anchor it to the vessel.

Unsheathing the device from the delivery catheter proved difficult at times in some embodiments. Parts of the device and delivery cable lacked column strength, and as a result the delivery cable would buckle or bend. Switching to a stiffer delivery cable for other embodiments improved results.

Attempts to recapture fully expanded devices were unsuccessful in some embodiments. The devices were simply too large to fit inside the delivery catheter. Partial recapture (i.e. capturing half the device) was possible. Incorporating a metallic or polymeric frame around the devices may enable full recapturing in other embodiments.

Device-Ostium Apposition

Gaps between the device and LAA ostium were quantified via image processing. All device geometries were able to occlude at least 86% of the ostium, with a majority of devices able to occlude roughly 95% of the ostium. Peri-device flow has been observed in roughly 32% of patients, and is considered to be insignificant if the leak is <5 mm. In some embodiments, there are no gaps between the device and ostium in order to prevent any emboli from entering systemic circulation and to improve endothelialization.

Ostium geometry may limit the effectiveness of LAAC devices. To determine if the benchtop models geometry was aggressively difficult when compared to clinical cases the "irregularity index" was calculated. The irregularity index correlates ostium geometry to residual leaks. To calculate the irregularity index, the real and ideal areas of the ostium are first recorded. The real area of the ostium is measured with any image processing software. The ideal area is calculated by measuring the major and minor axes of the ostium and using the following equation: Ideal area=π·major radius·minor radius. The irregularity index is then calculated by the following equation: Irregularity=abs[1−(Ideal Area/ Real Area)]

An irregularity index of 0.04 was identified as a threshold to predict a leak with a specificity of 94%. The irregularity index of the benchtop model used herein was around 0.027, which means the geometry of the benchtop model is not particularly irregular. In other words, the benchtop models geometry should be suitable for treatment. Since the SEDs did not completely seal the ostium, they may need to be more over-sized to conform to the ostium.

Particulate Generation

Figure 25:
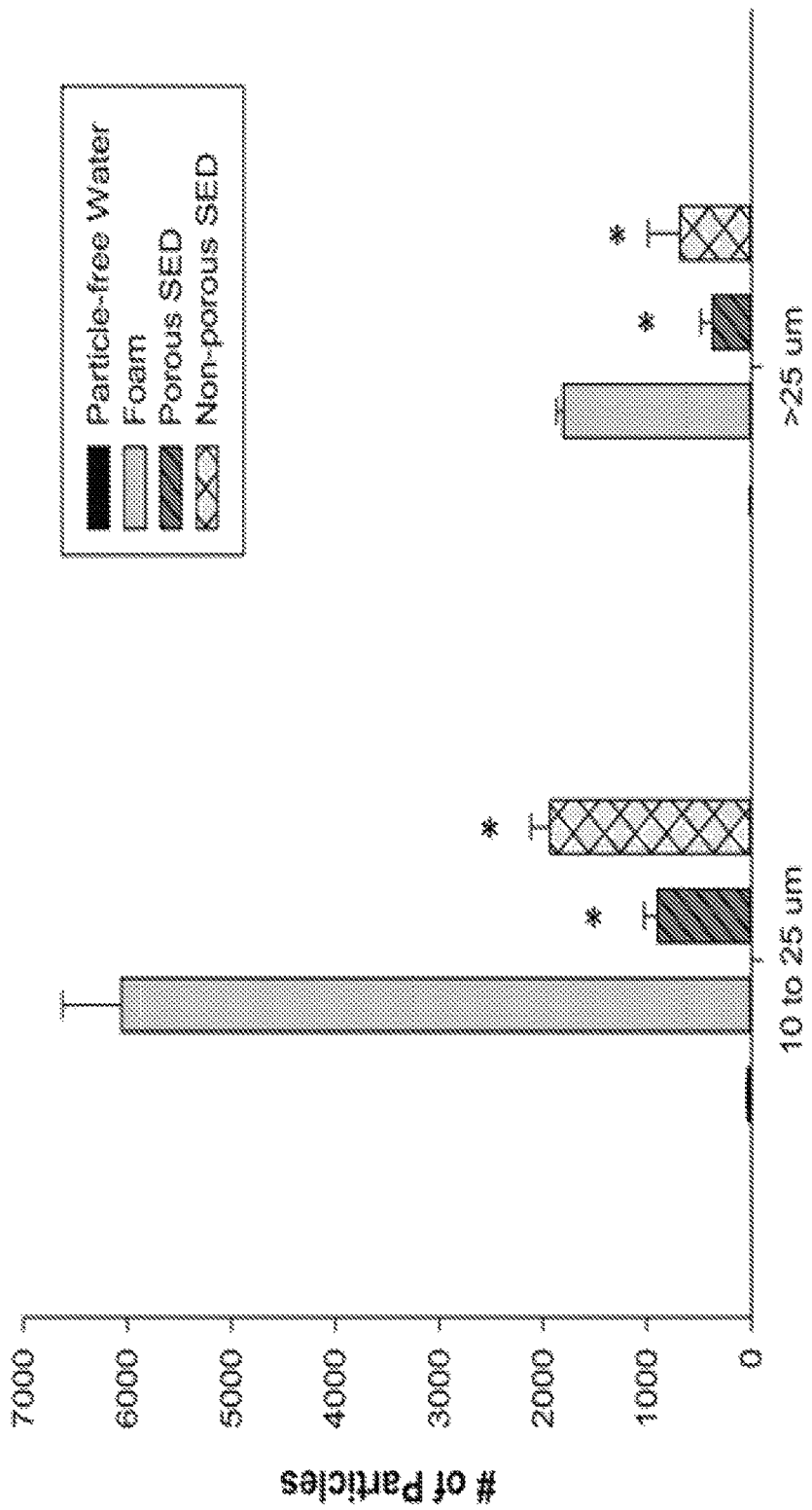
FIG. 25: Number of particulates counted from particle-free water, SMP foam, a non-porous embodiment, and a porous embodiment.

The distribution of particles is shown in FIGS. 24 and 25. The low amount of particles generated from particle-free water verifies the test environment is suitable for particulate analysis (limit≥10 μm=40, ≥25 μm=10). A significant reduction in the number of particles was observed when SMP foam was encapsulated in a membrane. The porous SEDs were compliant with the limits defined by the USP 788 light obscuration method (limit≥10 μm=6000, ≥25 μm=600). However, the porous SEDs were not compliant with the limits defined by the USP 788 microscopic method, despite being close (limit≥10 μm=3000, ≥25 μm=300). The devices would be compliant if they were cleaned and handled properly, and if the membrane pore size was decreased from 261 μm. Furthermore, the method of counting was performed with image analysis software that may have inflated the particle count.

An objective herein is to compare the particle levels between a foam and a SED, and verify if there was a reduction of particles. FIG. 25 shows a significant reduction of particles between foam and devices, highlighting the utility of encapsulating foams. Interestingly, the non-porous SED samples generated more particles than the porous SED samples. This result was unexpected, considering the non-porous SEDs should not allow any encapsulated foam particles from escaping. Potential causes for the discrepancy include the handling of the samples and membrane tears. All samples were handled in ambient air and crimped in a non-sterile stent crimper that was not cleaned between samples. Furthermore, the non-porous SEDs were air-tight and could have burst when crimped, similar to squeezing a balloon. The membrane was perforated with a needle a few times to prevent bursting, but could have been ineffective.

Figure 26B:
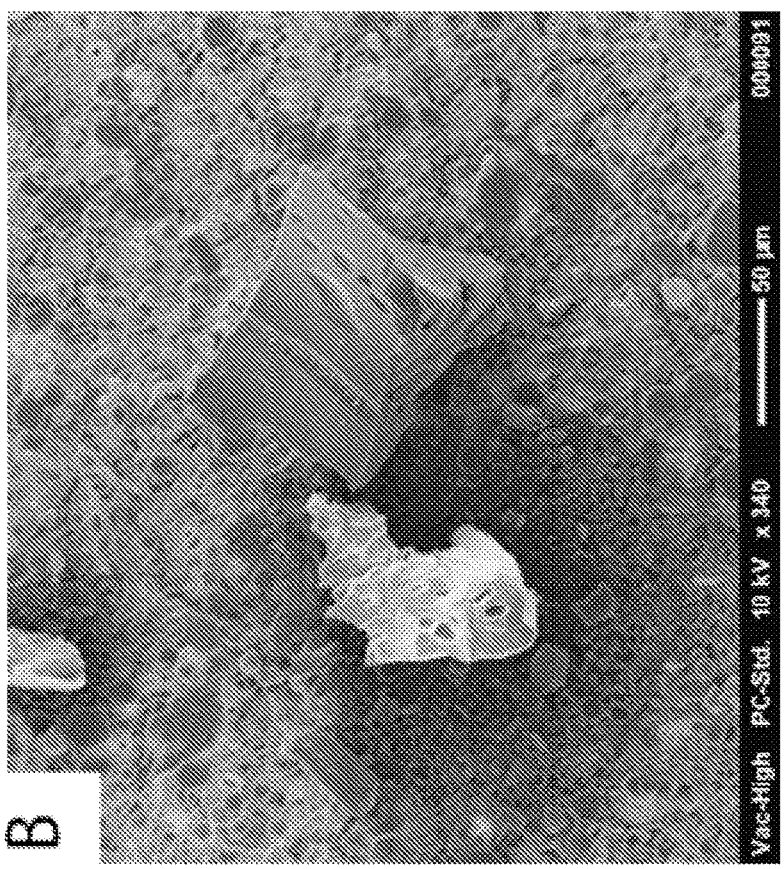
FIGS. 26(A) and (B): Images of a filter membrane.
Figure 26A:
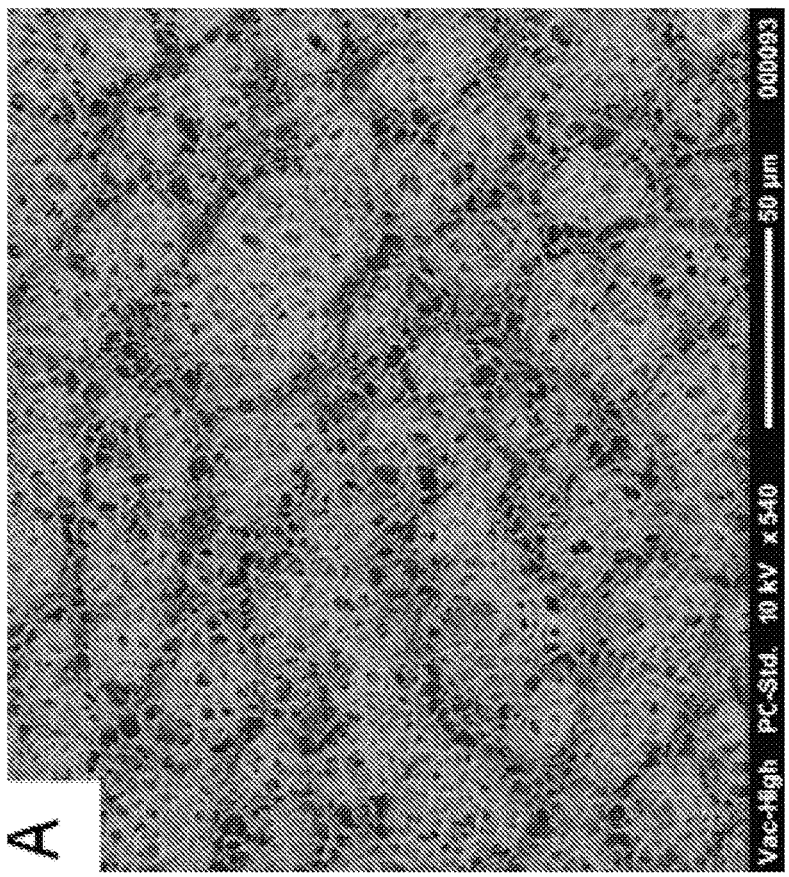

Based on SEM and light microscopy images, the largest particles were fractured struts that were long but narrow. Numerous particles composed of thin SMP cell membranes were also observed (FIGS. 26(A) and 26(B)). The SMP cell membranes were typically trapezoidal and came in many different sizes that were less than 200 μm. The amount of particles composed of cell membranes would be expected to drop if the SMP foam was reticulated and thoroughly washed.

Micro-embolization of cerebral arteries is an inherent risk for embolic protection devices and for the SEDs described herein. Studies have reported stroke victims show pathological evidence of occluded arterioles ranging from 50 to 300 μm. The danger of micro-embolization is further supported by a series of patients who developed neurologic dysfunction following a cardiac procedure. These patients died shortly after and autopsy revealed acellular material (<70 μm), believed to be emboli, deposited in their cerebral microvasculature. Despite the risk of micro-embolization, the SEDs reduce the risk of macro and micro-embolization relative to a non-encapsulated SMP foam. A reduction of the SED's membrane pore size, in conjunction with improved filter design and proper cleaning, is expected to improve the capture of particles.

4. CONCLUSIONS 4.1 Summary

SMP foams have been used in endovascular applications due to their ability to volumetrically fill body cavities after being deployed via catheter. These foams, however, pose a risk of generating harmful particulates that can cause unintended ischemia. The risk of generating harmful particulates is further increased when SMP foam is in contact with nitinol, or other hard materials that are common in endovascular devices. An objective of embodiments described herein was, therefore, to mitigate the risk of SMP foams generating particulates. To do this a SED was designed, fabricated, and tested in the context of closing LAAs. Left atrial appendage closure (LAAC) was chosen as the intended application for the device (in some embodiments, but not all embodiments) because predicate devices are composed of nitinol, and this device could be integrated with predicate devices.

The SMP foams used to develop SEDs were characterized. A main concern for the development of a SED for LAAC was determining a method to allow SMP foam to undergo a 10× diameter expansion. In some embodiments SMP foams were needed to expand to an OD of 30 mm following delivery from a 12 Fr catheter; which roughly corresponds to a 10× diameter expansion. To do this, cylindrical SMP foams were bored, or hollowed, in the center in an effort to increase the expansion ratios. Results showed that SMP foams were able to reach a 10× expansion when a 20 mm hole was punched through the center. Increasing the pore size and bore size increased the expansion ratio of SMP foam due to the decrease in foam density. Regardless of pore or bore size, all SMP foams were able to expand to 30 mm or greater from a compressed state when placed in body temperature water.

The final design chosen for an embodiment consisted of a SMP foam encapsulated in a porous TPU film that had stainless steel tubes epoxied to both ends. To deliver and deploy the SED, a simple screw-mechanism was designed and fabricated. TPU films were chemically, thermally, and morphologically characterized. ATR-FTIR confirmed the presence of polyurethane in the TPU films, and also revealed one of the films was a polyether-polyurethane film. DSC revealed the TPU films had a $T_g$ below freezing. The low $T_g$ allows the films to expand in tandem with SMP foam when placed into the body, however, it also means the films may not hold their crimped geometry. SEM analysis of the as-received TPU films revealed they were monolithic and impermeable to water. Thus, a $CO_2$ laser created uniform 261 μm pores into the TPU film to enable blood and cells to penetrate the SMP foam. The film was molded into a closed-end cylinder by placing wrapping it around foam and heat-sealing the ends. The stainless steel tubes epoxied to the ends of the device enable fluoroscopic imaging, and aid in delivering the device.

The ability for embodiments to be delivered via a 12 Fr catheter, occlude a LAA, reduce particles, and undergo actuation in blood and adsorb blood were evaluated. Devices were capable of fitting within a 12 Fr catheter. Crimped devices were submerged into citrated and activated bovine blood and showed excellent actuation, suggesting that under in-vivo conditions the device will actually expand to occlude the cavity. Devices also doubled their weight in adsorbed blood. Visual inspection revealed clotted bovine blood between the SMP foam and the TPU films, and that blood was able to penetrate deep within the foam. These results suggest that thrombus, in addition to SMP foam, may aid in occluding body cavities.

Devices were able to be successfully delivered into an anatomical model. Several observations were made that could improve device delivery. Accordingly embodiments include anchoring the device in the appendage, fabricating stiffer devices, and using a stiffer delivery cable. Gaps between the LAA ostium and devices were measured via image processing. Gaps between the device and ostium accounted for 4 to 14% of the ostium surface area.

A protocol based on USP 788 was adapted to count the number and size of particles that were generated as SMP foam actuated with or without a membrane. Results showed that encapsulating SMP foam in a TPU film significantly reduced the number of particles. SEM of the particles revealed troublesome particles composed of long and narrow foam struts, and thin cell membranes.

4.2 Considerations

There were many limitations throughout the development of these embodiments. To minimize the crimped diameter of the foam the centers were bored out. Sacrificing foam materials may inhibit healing, limit actuation, and reduce the radial expansion force of the foam. Limited actuation and radial expansion force could cause inadequate sealing and foam migration inside the body. Thus, other embodiments may omit the bores in the foams. An embodiment includes an alternative to boring out foam by increasing the crimping pressure. Various pressures are used for various embodiments to preserve the ability of water or blood to plasticize the foam.

Finding a suitable material to encapsulate the SMP foam was a difficult challenge. Initially, PET (i.e. Dacron) was investigated. However, the embodiment using PET was a stiff, non-elastic material that would not expand from a crimped state (but may be suitable in some embodiments). TPU films were then investigated and served their purpose and may be suitable in some embodiments. As received TPU films were not porous, and did not retain their crimped geometry for extended periods of time. Furthermore, processing the TPU films to form porous cylinders resulted in seam-lines, rough edges, and large pores. However, such embodiments may be suitable in various clinical scenarios. Some embodiments include synthesized porous SMP films with tailored transition temperatures. Embodiments of the SMP films include thermoset films. Various embodiments have various optimal porosities. In some embodiments these films are surface-modified to be non-thrombogenic or loaded with drugs or growth factors.

Following deployment of the SEDs in the benchtop model, it was observed the devices were not fixed and could easily migrate out of the appendage. To prevent device migration embodiments of the devices are augmented with super-elastic alloys or polymers, or coils.

A motivation of embodiments was to reduce the generation of foam particles due to interaction with nitinol and hard materials. Embodiments integrate SEDs with nitinol.

An embodiment includes a device to be used independently or in concert with other technology to selectively occlude vascular defects. An embodiment is comprised of a flexible thin polymer membrane that encapsulates SMP foam (or some other expanding agent in other embodiments, such as a hydrogel). The embodiment is able to be delivered endovascularly via catheter to the defect, wherein it is deployed and passively expanded to fill the surrounding volume. The flexible membrane can be perforated to allow blood and cellular infiltration into the porous SMP foam. The flexible membrane may also prevent large emboli from entering systemic circulation. Possible applications include occluding septal defects, aneurysms, LAAs, and other vascular defects. The technology may enable integration of SMP foams with existing technology, or metallic/polymeric components without increasing the risk of generating emboli.

Endovascular technology and therapies have experienced tremendous growth due to technology innovations, reimbursement, and preference for minimally invasive procedures. Embodiments described herein may contribute to this expanding market by improving devices to occlude vascular defects. In an embodiment the SMP foam allows for a 10× diameter expansion once deployed and improves volumetric filling of the vascular defect, which could reduce time of occlusion, procedural times, and improve healing. An embodiment incorporates a thin membrane that surrounds the SMP foam and protects the foam from generating potentially harmful particulates. Consequentially, this technology could enable shape-memory polymer foams to be integrated with existing technology and/or metallic/polymeric components, which otherwise could cause shearing of SMP foam and generate particulates. Thus, this technology enables commercial utility of SMP foams, improves occlusion of vascular defects, and mitigates the risk of particulates from entering a patient's systemic circulation.

There are numerous novel aspects of embodiments described herein.

First, in an embodiment the membrane allows the expanding foam to have voids (e.g. hollow foam shell) that enable volume expansions greater than the whole foam could expand. Hollowing out or coring out channels in the foam is a way to increase volume expansion. The combination of a void in the foam with the outer surface area of the foam covered in a membrane will permit the voids to clot more efficiently than compared to a foam with channels directly exposed to blood flow. Where 100× volume expansions are easily achievable with whole foams, the membrane covered foams may achieve 1000× or more. The shape recovery of the foam is important for the volume filling expansion as it forces the membrane to expand. The membrane alone, even if is a shape memory material, may not have the force to expand on its own in some embodiments.

Second, the membrane prevents particulates, including micro-clots, from escaping from the foam. When the foam alone is used in combinatorial devices where the foam is in contact with metal struts, especially if the metal struts are moving, the foam can shear off to form particulates. The membrane covering the foam acts as a barrier to prevent particulates from leaving the occlusion volume.

Third, the membrane may be made porous such that blood and fluids can enter the device but larger particulates cannot leave the volume. Any number of manufacturing methods can be used to create holes of uniform or varying diameters in the membrane. Further, the holes may be made in random or specific patterns. A primary purpose for these holes is to facilitate blood flowing into the volume. However, a secondary application is to allow drugs or therapeutics to flow out of the volume.

Fourth, the encapsulation of SMP foams with a thin flexible membrane causes stable occlusion of vascular defects. The SMP foam and thin flexible membrane are able to be radially compressed to fit within a delivery catheter, then expand once deployed into vasculature. The device is able to undergo a 10× diameter expansion, volumetrically occlude vascular defects, and mitigate the risk of generating emboli. Similar devices that incorporate membranes for vascular applications include embolic protection filters and vascular closure devices (e.g., LAAC devices). However, these devices do not occlude vasculature by volumetrically filling the cavity. Additionally, the membranes are expanded via shape-memory alloys (e.g., nitinol) or by balloon. This technology overcomes a technology gap for a device made of SMP foams to occlude vessels that also mitigates the risk of particulate generation.

An embodiment is comprised of SMP foam and a thin flexible membrane that encapsulates it. The SMP foam is synthesized and processed from isocyanates and alcohol monomers to form a polyurethane foam. The foam is then mechanically reticulated to create an interconnected porous architecture to allow blood and cellular infiltration that aids in the healing response. The foam is then cut into the desired geometry (i.e., hollow and non-hollow cylinders) and cleaned to remove potentially harmful chemical residues and particles. The foam is then freeze-dried and stored in dry conditions. A purpose of the foam is to volumetrically fill body cavities and promote a positive healing response.

Thin flexible membranes can be synthesized or purchased from third party suppliers. In an embodiment a thermoplastic polyurethane film (TPU; <30 microns thickness) is used to function as the membrane. The TPU film is perforated to become mesh-like. This is performed by making patterned holes on the film with a laser (pore diameter ~=260 microns; porosity=10.5%). The membrane is then heat-sealed to a desired geometry. In an embodiment this is performed by wrapping the membrane around the processed SMP foam. After wrapping the membrane around the foam, a seam is formed where the wrapped membrane meets. The seam is then heat-sealed by compressing the membrane together with aluminum plates and placing into a furnace at a specific time and temperature. Upon removal from the furnace, an encapsulated SMP foam is fabricated. Excess membrane material is then trimmed off. A purpose of the membrane is to protect the foam and capture potentially dangerous emboli.

The encapsulated SMP foam is then radially compressed (i.e., crimped) at specific temperatures and pressures. Following radial compression the device (i.e., encapsulated SMP foam) can then be pre-loaded into a delivery catheter. The device can then pushed into a body cavity with a pusher cable (i.e., guidewire, torque cable, etc.) wherein it undergoes passive actuation to expand and fill the cavity.

Another embodiment of the device includes integrating stainless steel bands to both ends of the device. This can be done through melt-processing or medical-grade epoxy. On one end, a pusher cable can be threaded into the stainless steel tube. The device can then be securely delivered and deployed to prevent procedural complications. Device retraction into the delivery catheter following deployment may also be possible.

In another embodiment, the device can be integrated with metallic/polymeric components. This could aid in device sealing, vessel wall apposition, device delivery, and prevent device migration.

In an embodiment synthesized membranes are processed to a desired geometry during synthesis, thus eliminating the need for perforating the membrane or heat-sealing it. The membrane may be formed with perforations such that perforations are not added at a later stage of processing. In an embodiment thermoplastic materials are blow-molded or thermally processed (e.g., injection molding) to the desired geometry. Porosity and pore pattern of the membrane can be further optimized. In an embodiment sealing of the membrane includes solvent welding.

Embodiment characterization shows that membranes that are beyond their glass transition temperature at body temperature are capable of expanding following compression. Materials that have glass transition temperature above body temperature, such as polyethylene terepthalate, may be too stiff and unable to expand following compression (but may be suitable in some embodiments). Initial testing shows that compressed devices (i.e., encapsulated SMP foam) are able to undergo a 10× diameter expansion. Certain device embodiments have a compressed outer diameter less than 3 mm and expand to 30 mm when placed in a water bath at body temperature. Following a protocol (USP 788), encapsulated devices were able to reduce the amount of particulates generated when compared to non-encapsulated devices. Stainless steel bands have been placed on the ends of the device to enable fluoroscopic imaging and allow for a screw-detachment mechanism.

In some embodiments the embolic foam includes a polyurethane SMP consisting of: N,N,N',N'-Tetrakis(2-hydroxypropyl)ethylenediamine (HPED), 2,2',2"-nitrilotriethanol (TEA), and 1,6-diisocyanatohexane (HDI). Residual chemicals may be present such as: catalysts (e.g. T-131 and BL-22) and surfactants (e.g. DC 198 and DC 5943). In the some embodiments the membrane includes the same material composition but may have the same or different Tg from that of the embolic foam. In an embodiment the membrane is thermoplastic ether and ester polyurethane film.

Thus, as described herein, endovascular embolization is an interventional procedure to seal off diseased vasculature from systemic circulation. SMP foams are a promising embolic material that can undergo shape change when exposed to stimuli, exhibit a positive healing response, and aid in rapid occlusion. SMP foams are porous materials that are comprised of struts and membranes that pose a risk of generating particles during device fabrication or delivery. Herein, a sheathed embolization device (SED) was designed, fabricated, and tested to occlude a LAA and to mitigate the generation of foam particles.

In an embodiment the SED consists of a thin polyurethane membrane that fully encapsulates the SMP foam (or partially encapsulates the foam in other embodiments), and is able to undergo shape change from a compressed state to an expanded state. Material properties of the device were characterized with differential scanning calorimetry, scanning electron microscopy, and Fourier transform infrared spectroscopy. The SED was tested in terms of its ability to occlude a patient-derived LAA model, its deliverability, and its ability to reduce particles.

Results from the studies demonstrate the SED's ability to be delivered minimally invasively, reduce particles, and occlude mock vasculature. Upon actuation in body-temperature fluid the SED achieved a 10× diameter expansion, making it ideal for endovascular applications. These results support using SEDs to occlude vasculature while mitigating the risk of unintended ischemia due to device-based particles. The results also support integrating the SED with third-party devices or components to develop functional embolization devices, such as LAAC devices.

Various examples of embodiments are now provided.

Example 1

An apparatus comprising: a first shape memory polymer (SMP) foam; a second SMP that encapsulates at least 50% of the outside surface of the first SMP foam.

Example 2

The apparatus of example 1 wherein the first SMP foam includes a thermoset SMP and the second SMP includes a thermoplastic SMP.

Example 3

The apparatus of example 2 comprising a membrane that includes the second SMP.

As used herein, a "membrane" includes a pliable sheet-like structure acting as a boundary, lining, or partition. Some embodiments may include membranes that cover 100%, 75%, 60%, 35%, or 20% of the exposed outer surfaces of the first SMP foam.

Example 4

The apparatus of example 3 including shape memory metal coupled to the first SMP foam and the second SMP.

Thus, some embodiments include a first unit that comprises a SMP foam and SMP membrane and no shape memory metal whereas other embodiments may include that same first unit coupled to a shape memory metal, such as a nitinol cage or skeleton or, more generally, structure.

While some embodiments include a shape memory metal surrounding (partially of fully) an embolic SMP foam with a membrane between the metal and the foam, other embodiments are not so limited. For example, in some embodiments the embolic foam surrounds (fully or partially) the SM metal and the membrane is between the SM metal and the foam. In other words, the membrane is not necessarily enveloping the film as long as the membrane helps protect SMP foam portions most likely to abrade and form particulates that could serve as emboli. Thus, the membrane may need to merely be between the SM metal and the embolic SMP foam considering the SM metal may abrade the foam. The membrane would not necessarily have to go around the entire foam so long as it separates the metal from the embolic foam. The metal may be inside, outside, or adjacent the foam so long as the membrane is between the metal and the embolic foam. For example, the membrane may coat the metal (e.g., an arm or spline of the SM metal) and thereby protect the embolic foam from the metal.

For example, a membrane may be between SM metal portions and the embolic foam. However, other membranes may also protect other portions of the same embolic foam (or other foams coupled to that foam) from, for example, the sheath walls. In such a case, for example, the most distal portion of the foam may not be covered by a membrane if that portion is not expected to experience high abrasion forces from the deployment conduit (catheter or sheath) or SM metal structure. Using partial membranes (instead of membranes that fully encapsulate embolic foams) may help deployment (expansion) of the embolic foam (by lowering the forces compressing the embolic foam).

In other embodiments, the protective outer membrane could be composed of a "skin" or "shell" of the SMP material that forms from contact between the reactive resin and foaming mold. This skin could be left intact or perforated with holes to increase liquid perfusion into the bulk foam.

The skin may have the same chemical composition as the embolic foam. For example, both may be formed from HPED, TEA, and HDI. However, the skin includes a layer of non-porous polymer and this layer is formed around the outside of the embolic foam. The skin forms at the boundary layers between the embolic foam and the mold (e.g., a container in which the embolic foam is formed) or open air (e.g., if the foam is formed in a uncovered container (e.g., beaker or bucket) then the foam may interface during its growth) because the bubbles of the foam coalesce and form a layer of solid material.

Example 5

The apparatus of example 4 wherein the shape memory metal includes nitinol.

Example 6

The apparatus of example 4 comprising a mesh that is formed from the shape memory metal.

Example 7

The apparatus of example 3 wherein the membrane is perforated over at least 50% of its outermost surface.

However, other embodiments may be perforated over 30, 40, 60, 70, 80, or 90% of the outer surface of the membrane. The perforations may be laser cut and include cauterized edges.

Example 8

The apparatus of example 7 wherein the second SMP includes a foam.

Example 9

The apparatus of example 3 wherein the first SMP foam is an open cell foam that is reticulated.

Example 10

The apparatus of example 9 wherein the first SMP foam is an open cell foam that is mechanically reticulated.

Example 11

The apparatus of example 3 wherein both of the first SMP foam and the second SMP include urethane.

Example 12

The apparatus of example 11 wherein (a) the first SMP includes a glass transition temperature (Tg) above 30 degrees C., and (b) the second SMP includes a Tg less than 30 degrees C.

Example 13

The apparatus of example 4 wherein the shape memory metal includes a plurality of anchors configured to implant the apparatus in tissue.

Example 14

The apparatus of example 3 wherein the first SMP foam is arranged in a cylindrical shape.

Example 15

The apparatus of example 14 the cylindrical shape is toroidal with a hollow central void.

Example 16

The apparatus of example 3 wherein the second SMP includes a heat sealed seam fixedly coupling first and second portions of the second SMP to one another.

Example 17

The apparatus of example 6 wherein at least a portion of the mesh forms a cup and at least a portion of the membrane is included within the cup.

Example 18

The apparatus of example 6 wherein at least a portion of the mesh forms a hemispherical shape and at least a portion of the membrane is included within the hemispherical shape. For example, a hemispherical shape may look like a cup.

Example 19

The apparatus of example 18 wherein an axis traverses (a) first and second portions of the acetabular shaped mesh, (b) first and second portions of the membrane, and (c) the first SMP foam.

Example 20

The apparatus of example 3 wherein a thickness of the membrane is between 10 and 40 microns.

Example 21

The apparatus of example 7 wherein an intermodal distance between two adjacent perforations is between 20 and 90 microns.

Example 22

An apparatus comprising: a first shape memory polymer (SMP) foam; a membrane that encapsulates at least 50% of the outside surface of the first SMP foam; wherein the membrane includes at least one member selected from the group consisting of Polyester, PTFE, FEP, UHMWPE, Polyurethane, PET, ePTFE, Poly(carbonate), Nylon, and combinations thereof.

As mentioned above, the membrane and embolic foam may have the same chemical components but the membrane may be tougher than the embolic foam. Regarding toughness and other physical attributes of the embolic foam and/or membrane, the mechanical properties of thermoplastic polyurethane (TPU) film and non-cleaned and non-reticulated H40 foams were investigated. The pore sizes of the foams ranged from small, medium, and large; which corresponded to 1000, 1500, and 1800 μm pore sizes, respectively. The mechanical properties of the TPU films were taken from the manufacturer's website, whereas the mechanical properties of foam were characterized following the ASTM D638 standard for non-rigid samples.

To characterize the foams they were first sliced to a thickness ≤4 mm A calibrated and certified ASTM D638 Type IV cutter (Pioneer-Dietecs Corporation, Weymouth Mass.) was used to punch dog bone samples from the foam slices. The ends of the dog bone samples were then epoxied to wooden stubs so they can be attached to the tensile tester's grips. The dog bone samples were then allowed to dry overnight in a vacuum oven. Dried dog bone samples were then loaded onto an Insight 30 material tester (Materials Testing Solutions, MTS Systems Corporation, Eden Prairie, Minn.), and strained until failure. Each composition was tested at least four times for reproducibility.

FIGS. 27 and 28 summarize the key mechanical properties for TPU film and H40 foam, respectively. The TPU film and H40 foam had similar tensile strengths. Foam pore size significantly affected the strain at break and modulus of foam. Foams with a smaller pore size possessed a lower modulus and were more flexible in a dry state when compared to their larger pore counterparts. Therefore, a small pore foam may enable easier delivery through tortuous anatomy and not fracture as readily. Fracture may occur under extreme strain of the foam, which may occur as the foam is retracted into the catheter. However, no conclusions can be determined at this time since these results reflect the mechanical properties of dry, non-processed foam, and not the mechanical properties of the wet, processed foam used in the clinical setting.

Example 1a

An apparatus comprising: a shape memory polymer (SMP) foam having an outside surface; and a membrane that encapsulates at least 50% of the outside surface of the SMP foam; wherein (a) the SMP foam includes a thermoset SMP, and (b) the membrane includes a thermoplastic polymer.

By "encapsulate" such an embodiment may include, for example, a band that goes around some or all of an outer perimeter of a SMP foam plug. However, proximal and distal ends of the plug may not be covered or encapsulated by the membrane. Thus, "encapsulate" does not necessarily mean to fully enclose.

The thermoplastic polymer may have very little to no shape memory in some embodiments.

Example 2a

The apparatus of example 1a including a shape memory (SM) metal coupled to the SMP foam and the membrane, wherein the membrane is between the SMP foam and the SM metal.

For example, an embodiment may include a nickel-titanium alloy stent. The SMP foam may be on the outside of the stent. The membrane may be between the stent and foam to prevent abrasion of the foam by the stent.

Example 3a

The apparatus of example 1a including a shape memory (SM) metal coupled to the SMP foam and the membrane, wherein the SM metal is between the SMP foam and the membrane.

For example, see FIG. 29. FIG. 29 provides a nickel-titanium alloy frame outside of the membrane (where the membrane is outside the embolic foam). The frame includes anchors to anchor the frame within the LAA.

The membrane may cover only a portion of the SM metal and/or only a portion of the foam.

Example 4a

The apparatus of example 1a including a shape memory (SM) metal coupled to the SMP foam and the membrane, wherein the SMP foam is between the membrane and the SM metal.

For instance, a foam may surround a SM metal stent. A membrane may surround the foam.

Example 5a

The apparatus according to any one of examples 2a to 4a comprising a stent, wherein the stent includes the SM metal.

Example 6a

The apparatus according to any one of examples 2a to 4a comprising a frame, wherein the frame includes the SM metal.

Example 7a

The apparatus of example 6a wherein the frame comprises a mesh.

Example 8a

The apparatus of example 6a wherein the frame includes a cavity and the cavity includes the SMP foam.

For instance, see FIG. 29.

Example 9a

The apparatus according to any of examples 1a to 8a wherein the membrane is perforated.

Example 10a

The apparatus of example 9a comprising at least 20 perforations, wherein each of the at least 20 perforations couples opposing surfaces of the membrane to one another.

For example, see FIG. 18(A).

Example 11a

The apparatus of example 10a wherein each of the at least 20 perforations includes a diameter greater than 150 microns.

Example 12a

The apparatus according to any of examples 11a to 12a, wherein an intermodal distance between two adjacent perforations of the at least 20 perforations is between 20 and 90 microns.

Example 13a

The apparatus according to any of examples 1a to 12a wherein: the SMP foam is a reticulated open-cell polyurethane foam; the SMP foam includes hydroxypropyl ethylenediamine (HPED), triethanolamine (TEA), and hexamethylene diisocynate (HDI).

Example 14a

The apparatus according to any of examples 2a to 13a comprising a plurality of mechanical anchors coupled to the SM metal, wherein the plurality of anchors are configured to implant the apparatus in tissue.

Example 15a

The apparatus according to any one of examples 2a to 14a wherein: an axis traverses (a) first and second portions of the SM metal, (b) first and second portions of the membrane, and (c) the SMP foam; the SMP foam is between the first and second portions of the SM metal; the SMP foam is between the first and second portions of the membrane.

For example, see the axis in FIG. 29.

Example 16a

The apparatus according to any one of examples 2a to 15a wherein a thickness of the membrane is between 10 and 40 microns.

Example 17a

An apparatus comprising: a thermoset shape memory polymer (SMP) foam; a membrane; and a shape memory (SM) metal; wherein the membrane includes at least one member selected from the group consisting of polyethylene terephthalate (polyester), polytetrafluoroethylene (PTFE), extruded PTFE (ePTFE), ultra-high-molecular-weight polyethylene (UHMWPE), polyurethane, poly(p-xylylene), nylon, poly(carbonate), fluorinated ethylene propylene (FEP), polyamide, polyether, polyethylene, polyethylene terephthalate (PET), polypropylene, or combinations thereof.

The membrane may or may not be a thermoplastic polymer.

Another version of Example 17a. An apparatus comprising: a shape memory material; a membrane; and a shape memory (SM) frame; wherein the membrane includes at least one member selected from the group consisting of polyethylene terephthalate (polyester), polytetrafluoroethylene (PTFE), extruded PTFE (ePTFE), ultra-high-molecular-weight polyethylene (UHMWPE), polyurethane, poly(p-xylylene), nylon, poly(carbonate), fluorinated ethylene propylene (FEP), polyamide, polyether, polyethylene, polyethylene terephthalate (PET), polypropylene, or combinations thereof.

Thus, not all embodiments require the embolic element to include a SMP, much less a SMP foam. Further, not all embodiments require a frame made of SM metal.

Example 18a

The apparatus of example 17a wherein: the SMP foam includes hydroxypropyl ethylenediamine (HPED), triethanolamine (TEA), and hexamethylene diisocynate (HDI); the membrane includes HPED, TEA, and HDI; the SMP foam is porous; and the membrane is not a foam.

For example, the membrane may include a skin as addressed above. The skin may be tougher than the embolic foam. Toughness may be determined as shown in FIG. 28(A).

Example 19a

The apparatus according to any of examples 17a to 18a, wherein the membrane comprises perforations, each of the perforations coupling opposing surfaces of the membrane to one another.

These perforations may not be inherent to the membrane but may instead be formed using a laser, mechanical perforation via needle or punch, and the like.

Example 20a

The apparatus according to any of examples 17a to 19a, wherein the membrane includes fibers.

Example 21a

The apparatus according to any of examples 17a to 20a wherein (a) the membrane directly contacts the SMP foam, and (b) the membrane directly contacts the SM metal.

Example 22a

The apparatus of example 21a wherein the membrane completely surrounds a portion of the SM metal.

For instance, the membrane may encircle a strut. In FIG. 29, the membrane may coat the struts of the frame. Another membrane may enclose the foam or the "another membrane" may be omitted in light of the membrane that coats the struts of the frame. The coating of the frame with the membrane may be performed in a manner similar to vinyl coated crab traps.

Example 23a

The apparatus according to any of examples 17a to 22a comprising an additional membrane, wherein the membrane includes at least one member selected from the group consisting of polyester, PTFE, ePTFE, UHMWPE, polyurethane, poly(p-xylylene), nylon, poly(carbonate), FEP, polyamide, polyether, polyethylene, PET, polypropylene, or combinations thereof.

Example 24a

The apparatus of example 23a wherein the additional membrane directly contacts the SMP foam.

Example 25a

The apparatus according to any of examples 17a to 24a comprising a plurality of mechanical anchors coupled to the SM metal, wherein the plurality of anchors are configured to implant the apparatus in tissue.

The above examples illustrate embodiments applicable for any SMP foam occlusion device, and particularly for devices under significant mechanical stress. Structural heart applications such as LAA occlusion, and foams on transcatheter heart valves to reduce perivalvular leak, are examples of vascular device applications with significant mechanical loading. A function of the membrane is to limit particulates from escaping downstream during acute delivery. Once a stable thrombus integrates into the foam, the risk of particulation drops significantly. In an embodiment, the membrane is porous enough for sufficient blood permeability to create a thrombus throughout the foam and membrane structure. The fibrin crosslinked clot will be physically incorporated into the porous structure of the foam and membrane to prevent the developing clot from breaking off and causing embolic events.

In addition to limiting particulation, material selection and surface treatments may be included on the membrane to increase the lubricity of the compressed device while being delivered through the catheter.

As mentioned above, the membrane may encapsulate the foam to capture particulates, but may also form a protective interface between the SMP foam and other device or tissue boundaries that could potentially abrade or damage the foam during delivery or implantation. For example, the membrane may be (a) on the internal and external diameters of a foam annulus, (b) between a metal stent and exterior foam, or (c) as a sheath over a cylindrical foam plug.

Porosity can be introduced to the membrane by: (a) making the film from a porous electrospun fiber mat (see Example 20a), (b) using laser machining to introduce holes in a solid polymer membrane, (c) mechanical membrane perforation, (d) supercritical gas foaming of thermoplastic membranes to introduce porosity, or (e) some combination thereof. For example, the fibers may include HDI, HPED, and TEA. The fibers may be electrospun such that fibers inherently have pores between two or more adjacent fibers. The "membrane" may also be a native skin that develops on the surface of the SMP polyurethane foam during manufacturing. Although not inherently porous, this skin may be made porous with, for example, mechanical and laser techniques addressed above.

In an embodiment the membrane covering does not necessarily require shape memory properties. Thin or especially compliant membranes are flexible enough to not encumber the underlying expanding SMP foam. This allows for the use of thermoplastic membranes and films made with traditional techniques (e.g., thermoforming, film blowing, electrospinning, dip coating, and the like)

In an embodiment the membrane includes polyurethane (either thermoplastic, or thermoset with a composition similar to the internal embolic SMP foam), or other thermoplastic polymer compositions including polyethylene, polypropylene, polyester, ePTFE, PET, polyamide, polyether, or some combination thereof.

The membrane may adhere to a SMP foam and/or SM metal frame via an adhesive, such as a polyurethane based adhesive.

In the description of various embodiments, numerous specific details are set forth but embodiments of the invention may be practiced without these specific details. Well-known structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner.

The invention claimed is:

1. An apparatus comprising:
a thermoset shape memory polymer (SMP) foam having proximal and distal ends;
a thermoplastic membrane film that: (a) encircles a middle portion of the SMP foam, and (b) covers at least one of the proximal or distal ends of the SMP foam; and
a shape memory (SM) metal;
wherein the thermoplastic membrane film includes at least one member selected from the group consisting of polyethylene terephthalate (polyester), polytetrafluoroethylene (PTFE), extruded PTFE (ePTFE), ultra-high-molecular-weight polyethylene (UHMWPE), polyurethane, poly(p-xylylene), nylon, poly(carbonate), fluorinated ethylene propylene (FEP), polyamide, polyether, polyethylene, polyethylene terephthalate (PET), polypropylene, or combinations thereof; and the SMP foam includes a polymer that comprises polymerized monomers, the monomers including hydroxypropyl ethylenediamine (HPED), triethanolamine (TEA), and hexamethylene diisocynate (HDI).

2. The apparatus of claim 1 wherein:
the SMP foam is porous; and
the thermoplastic membrane film is not a foam.

3. The apparatus of claim 1, wherein the thermoplastic membrane film comprises perforations, each of the perforations coupling opposing surfaces of the thermoplastic membrane film to one another.

4. The apparatus of claim 1 wherein (a) the thermoplastic membrane film directly contacts the SMP foam, and (b) the thermoplastic membrane film directly contacts the SM metal.

5. The apparatus of claim 1 comprising a plurality of mechanical anchors coupled to the SM metal, wherein the plurality of anchors is configured to implant the apparatus in tissue.

6. The apparatus of claim 1 wherein the thermoplastic membrane film is configured to undergo compression and expansion alongside the SMP foam.

7. The apparatus of claim 1 wherein the thermoplastic membrane film is configured to expand in response to expansion of the SMP foam.

8. The apparatus of claim 1 wherein the thermoplastic membrane film is configured to degrade following endothelialization of the SMP foam.

9. The apparatus of claim 1, wherein a thickness of the thermoplastic membrane film is between 10 and 40 microns.

* * * * *